(12) United States Patent
Horikoshi et al.

(10) Patent No.: US 9,066,517 B2
(45) Date of Patent: Jun. 30, 2015

(54) PEST CONTROL AGENTS FOR HONEYBEE PARASITIC PESTS, AND PEST CONTROL METHOD FOR HONEYBEE PARASITIC PESTS USING THE PEST CONTROL AGENTS

(71) Applicant: MEIJI SEIKA PHARMA CO., LTD., Tokyo (JP)

(72) Inventors: Ryo Horikoshi, Yokohama (JP); Masaaki Mitomi, Yokohama (JP)

(73) Assignee: MEIJI SEIKA PHARMA CO., LTD., Tokyo (JP)

( * ) Notice: Subject to any disclaimer, the term of this patent is extended or adjusted under 35 U.S.C. 154(b) by 0 days.

(21) Appl. No.: 14/537,378

(22) Filed: Nov. 10, 2014

(65) Prior Publication Data
US 2015/0057288 A1    Feb. 26, 2015

Related U.S. Application Data

(63) Continuation of application No. PCT/JP2014/063916, filed on May 27, 2014.

(30) Foreign Application Priority Data

May 27, 2013 (JP) ................................ 2013-110778

(51) Int. Cl.
| | | |
|---|---|---|
| A61K 31/50 | (2006.01) | |
| A01N 43/82 | (2006.01) | |
| A01N 25/02 | (2006.01) | |
| A01N 43/40 | (2006.01) | |
| A01M 1/20 | (2006.01) | |
| A01N 43/42 | (2006.01) | |
| A01N 43/54 | (2006.01) | |
| A01N 43/58 | (2006.01) | |
| A01N 43/60 | (2006.01) | |
| A01N 43/78 | (2006.01) | |
| C07D 401/06 | (2006.01) | |
| C07D 417/06 | (2006.01) | |

(52) U.S. Cl.
CPC ............... *A01N 43/82* (2013.01); *A01N 25/02* (2013.01); *A01N 43/40* (2013.01); *A01M 1/20* (2013.01); *A01N 43/42* (2013.01); *A01N 43/54* (2013.01); *A01N 43/58* (2013.01); *A01N 43/60* (2013.01); *A01N 43/78* (2013.01); *C07D 401/06* (2013.01); *C07D 417/06* (2013.01)

(58) Field of Classification Search
None
See application file for complete search history.

(56) References Cited

U.S. PATENT DOCUMENTS

| | | | |
|---|---|---|---|
| 4,803,277 A | 2/1989 | Shiokawa et al. | |
| 4,876,265 A | 10/1989 | Schmid | |
| 5,250,498 A * | 10/1993 | Andree et al. | 504/105 |
| 2013/0150414 A1 | 6/2013 | Kagabu et al. | |
| 2013/0165482 A1 | 6/2013 | Kagabu et al. | |
| 2014/0135281 A1 | 5/2014 | Fougeroux | |
| 2015/0005347 A1 | 1/2015 | Kagabu et al. | |

FOREIGN PATENT DOCUMENTS

| | | |
|---|---|---|
| DE | 3407042 A1 | 9/1985 |
| EP | 0 259 738 A2 | 3/1988 |
| EP | 0 432 600 A2 | 6/1991 |
| EP | 0 639 569 A1 | 2/1995 |
| JP | 59-199610 A | 11/1984 |
| JP | 63-150275 A | 6/1988 |
| JP | 5-78323 A | 3/1993 |
| JP | 2012-140449 A | 7/2012 |
| JP | 4993641 B2 | 8/2012 |
| WO | 2012/029672 A1 | 3/2012 |
| WO | 2012/156342 A1 | 11/2012 |
| WO | 2012/156344 A1 | 11/2012 |
| WO | 2013/129692 A2 | 9/2013 |

OTHER PUBLICATIONS

Krohnke, F. et al., Chemische Berichte (1955), 88,II03-8.*
Besard et al., Compatibility of traditional and novel acaricides with bumblebees (*Bombus terrestris*): a first laboratory assessment of toxicity and sublethal effects, Pest Management and Science, 2010, V66, p. 786-793.
Chemische Berichte (1955), 88, 1103-8, Cited in Specification filed Nov. 10, 2014.
Kagaku to Seibutsu (Bioscience & Biotechnology), 2010, vol. 48, No. 8, pp. 577-582, Y; cited in Specification filed Nov. 10, 2014.
International Search Report dated Aug. 12, 2014, issued in counterpart International application No. PCT/JP2014/063916.

* cited by examiner

*Primary Examiner* — Heidi Reese
(74) *Attorney, Agent, or Firm* — Sughrue Mion, PLLC

(57) ABSTRACT

A pest control method for honeybee parasitic pests has been found, which is highly safe to honeybees and demonstrates excellent pest control effects against honeybee parasitic pests by using a honeybee parasitic pest control agent containing at least one of a compound represented by Formula (I) and acid addition salts thereof.

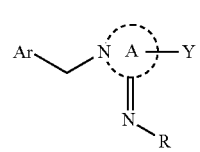

(I)

13 Claims, No Drawings

PEST CONTROL AGENTS FOR HONEYBEE PARASITIC PESTS, AND PEST CONTROL METHOD FOR HONEYBEE PARASITIC PESTS USING THE PEST CONTROL AGENTS

BACKGROUND OF THE INVENTION

1. Field of the Invention

The present invention relates to pest control agents for controlling pests such as honeybee parasitic pests, and a pest control method using the pest control agents.

2. Related Background Art

Not only are honeybees used for collecting honey, but also the use ratio as beneficial pollinator insects is now increasing. It has been reported that the annual economic value of honeybee pollination has reached 5 to 10 billion dollars in the United States and is expected to be 100 or more times the economic value of honeybee products including honey. The number of colonies of bees kept at present is 9 million in China, 9 million in the regions of the former Soviet Union, 3 million in the United States, 3 million in Mexico, 2 million in Brazil, 1.50 million in Argentina, and 0.20 million in Japan. Thus, the beekeeping industry is one of important sectors of agriculture in any countries in the world.

Recently, Colony Collapse Disorder (CCD) has become a problem worldwide, and serious influences on the beekeeping industry due to the decrease in the number of honeybee colonies have been reported. It is said that Colony Collapse Disorder is attributable to adverse influences on honeybees from honeybee parasitic pests including *Varroa destructor* (Kagaku to Seibutsu (Bioscience & Biotechnology), 2010, vol. 48, no. 8, pp. 577 to 582 (NPL 1)), neonicotinoid-based chemicals, or the like.

At present, amitraz, fluvalinate, coumaphos, formic acid, sucrose octanoate ester, organic acids such as β-acid, and the like are known as chemicals for *Varroa destructor* control. In addition, chemicals under studies include a triazine-based insecticide cyromazine (International Publication No. WO2012/156342 (PTL 1)), a hydrazine-based insecticide bifenazate (International Publication No. WO2012/156344 (PTL 2)), and the like. However, the number of chemicals highly safe to honeybees is still small, and there are problems of parasitic pests resistant to insecticides. Hence, a chemical for honeybee parasitic pest control having a novel action and high safety is strongly desired.

In such circumstances, a novel chemical for honeybee parasitic pest control has been further searched for. A compound of the present invention includes a compound described as a pest control agent in Japanese Patent No. 4993641 (PTL 3) and International Publication No. WO2013/129692 (PTL 4). However, the literatures do not state at all that the pest control agent has an effect against honeybee parasitic pests. Moreover, European Patent Application Laid-Open No. 432600 (PTL 5) discloses a compound having a structure similar to the compound of the present invention, but fails to provide any description or suggestion regarding safety to honeybees and effect against honeybee parasitic pests.

Further, Japanese Unexamined Patent Application Publication No. Hei 5-78323 (PTL 6) and European Patent Application Laid-Open No. 268915 (PTL 7) disclose a structural formula of N-[1-((6-chloropyridin-3-yl)methyl)pyridine-2(1H)-ylidene]-2,2,2-trifluoroacetamide, but fail to provide any description or suggestion regarding safety to honeybees and effect against honeybee parasitic pests.

Chemische Berichte (1955), 88, 1103-8 (NPL 2) discloses a plurality of compounds having a ring structure similar to the compound of the present invention, but the compounds are disclosed only as synthetic intermediates.

European Patent Application Laid-Open No. 259738 (PTL 8) discloses a plurality of compounds having a ring structure similar to the compound of the present invention, but fails to disclose or suggest a compound having a trifluoroacetic acid imino structure.

SUMMARY OF THE INVENTION

An object of the present invention is to provide an excellent pest control method for honeybee parasitic pests by using a chemical having high safety to honeybees and novel actions.

In order to solve the problems, the present inventors have intensively studied, and as a result, have found that a compound represented by the following Formula (I) shows excellent pest control effects against honeybee parasitic pests. The present invention is based on the finding.

Therefore, the present invention provides a honeybee parasitic pest control agent containing at least one of a compound represented by the following Formula (I) and acid addition salts thereof, as well as a method for controlling honeybee parasitic pests by using the pest control agent.

Specifically, the present invention provides the following aspects.

(1) A honeybee parasitic pest control agent, comprising:

at least one of a compound represented by the following Formula (I) or acid addition salts thereof as an active ingredient.

[in the formula (I), Ar represents a phenyl group which may be substituted, a 5- to 6-membered heterocycle which may be substituted, or a 4- to 10-membered heterocycloalkyl group, A represents a 5- to 10-membered heterocycle having a unsaturated bond including one or more nitrogen atoms, and has an imino group substituted with an R group at a position adjacent to the nitrogen atom present on the cycle, Y represents a hydrogen atom, a halogen atom, a hydroxyl group, a C1 to C6 alkyl group which may be substituted with a halogen atom, a C1 to C6 alkyloxy group which may be substituted with a halogen atom, a cyano group, or a nitro group, and R represents any one of groups represented by the following Formulae (a) to (e), (y) or (z),

-continued

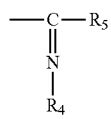
(d)

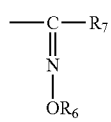
(e)

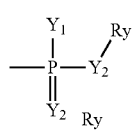
(y)

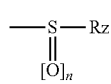
(z)

here, $R_1$ represents a hydrogen atom, a substituted C1 to C6 alkyl group, a C2 to C6 alkenyl group which may be substituted with a halogen atom, a C2 to C6 alkynyl group which may be substituted with a halogen atom, or a pentafluorophenyl group, $R_2$ represents a C1 to C6 alkyl group which may be substituted with a halogen atom, an unsubstituted C3 to C6 branched or cyclic alkyl group, a C2 to C6 alkenyl group which may be substituted with a halogen atom, a C2 to C6 alkynyl group which may be substituted with a halogen atom, a substituted or unsubstituted (C6 to C10) aryl group, a substituted or unsubstituted 5- to 10-membered heterocycle, or a substituted or unsubstituted benzyl group, $R_3$ represents a C1 to C6 alkyl group which may be substituted with a halogen atom, a C2 to C6 alkenyl group which may be substituted with a halogen atom, a C2 to C6 alkynyl group which may be substituted with a halogen atom, a substituted or unsubstituted (C6 to C10) aryl group, a substituted or unsubstituted (C6 to C10) aryl (C1 to C6) alkyl group, a substituted or unsubstituted (C6 to C10) aryl (C2 to C6) alkenyl group, a substituted or unsubstituted (C6 to C10) aryl (C2 to C6) alkynyl group, a substituted or unsubstituted phenoxy (C1 to C6) alkyl group, a substituted or unsubstituted phenoxy (C2 to C6) alkenyl group, a substituted or unsubstituted phenoxy (C2 to C6) alkynyl group, a substituted or unsubstituted 5- to 10-membered heterocycle, a substituted or unsubstituted 5- to 10-membered heterocycle (C1 to C6) alkyl group, a substituted or unsubstituted 5- to 10-membered heterocycle (C2 to C6) alkenyl group, a substituted or unsubstituted 5- to 10-membered heterocycle (C2 to C6) alkynyl group, a (C1 to C4) alkoxy (C1 to C5) alkyl group, a (C1 to C4) alkoxy (C2 to C5) alkenyl group, a (C1 to C4) alkoxy (C2 to C5) alkynyl group, a (C1 to C4) alkylthio (C1 to C5) alkyl group, a (C1 to C4) alkylthio (C2 to C5) alkenyl group, or a (C1 to C4) alkylthio (C2 to C5) alkynyl group, $R_4$ represents a hydrogen atom, a formyl group, a C1 to C18 alkyl group which may be substituted, a C2 to C6 alkenyl group which may be substituted with a halogen atom, a C2 to C6 alkynyl group which may be substituted with a halogen atom, a substituted or unsubstituted (C6 to C10) aryl group, a substituted or unsubstituted (C6 to C10) aryl (C1 to C6) alkyl group, a substituted or unsubstituted (C6 to C10) aryl (C2 to C6) alkenyl group, a substituted or unsubstituted (C6 to C10) aryl (C2 to C6) alkynyl group, a substituted or unsubstituted phenoxy (C1 to C6) alkyl group, a substituted or unsubstituted phenoxy (C2 to C6) alkenyl group, a substituted or unsubstituted phenoxy (C2 to C6) alkynyl group, a substituted or unsubstituted 5- to 10-membered heterocycle, a substituted or unsubstituted 5- to 10-membered heterocycle (C1 to C6) alkyl group, a substituted or unsubstituted 5- to 10-membered heterocycle (C2 to C6) alkenyl group, a substituted or unsubstituted 5- to 10-membered heterocycle (C2 to C6) alkynyl group, a (C1 to C4) alkoxy (C1 to C5) alkyl group, a (C1 to C4) alkoxy (C2 to C5) alkenyl group, a (C1 to C4) alkoxy (C2 to C5) alkynyl group, a (C1 to C4) alkylthio (C1 to C5) alkyl group, a (C1 to C4) alkylthio (C2 to C5) alkenyl group, a (C1 to C4) alkylthio (C2 to C5) alkynyl group, or a group represented by the following Formulae (f) to (n)

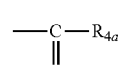
(f)

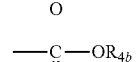
(g)

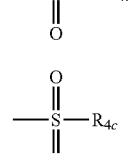
(h)

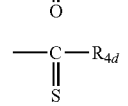
(i)

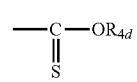
(j)

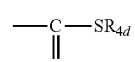
(k)

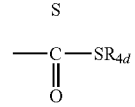
(l)

(m)

(n)

[here, $R_{4a}$, $R_{4b}$ and $R_{4c}$ represent a C1 to C6 alkyl group which may be substituted with a halogen atom, a C2 to C6 alkenyl group which may be substituted with a halogen atom, a C2 to C6 alkynyl group which may be substituted with a halogen atom, a substituted or unsubstituted (C6 to C10) aryl group, a substituted or unsubstituted (C6 to C10) aryl (C1 to C6) alkyl group, a substituted or unsubstituted (C6 to C10) aryl (C2 to C6) alkenyl group, a substituted or unsubstituted (C6 to C10) aryl (C2 to C6) alkynyl group, a substituted or unsubstituted phenoxy (C1 to C6) alkyl group, a substituted or unsubstituted phenoxy (C2 to C6) alkenyl group, a substituted or unsubstituted phenoxy (C2 to C6) alkynyl group, a substituted or unsubstituted 5- to 10-membered heterocycle, a substituted or unsubstituted 5- to 10-membered heterocycle (C1 to C6) alkyl group, a substituted or unsubstituted 5- to 10-membered heterocycle (C2 to C6) alkenyl group, a substituted or unsubstituted 5- to 10-membered heterocycle (C2 to C6) alkynyl group, a (C1 to C4) alkoxy (C1 to C5) alkyl group, a (C1 to C4) alkoxy (C2 to C5) alkenyl group, a (C1 to C4) alkoxy (C2 to C5) alkynyl group, a (C1 to C4) alkylthio (C1 to C5) alkyl group, a (C1 to C4) alkylthio (C2 to C5) alkenyl group, or a (C1 to C4) alkylthio (C2 to C5) alkynyl group, $R_{4d}$ represents a C1 to C6 alkyl group which may be substituted with a halogen atom, a C2 to C6 alkenyl group which may be substituted with a halogen atom, a C2 to C6 alkynyl group which may be substituted with a halogen atom, a substituted or unsubstituted (C6 to C10) aryl group, or a substituted or unsubstituted 5- to 10-membered heterocycle, and $R_{4e}$ and $R_{4f}$ each independently represent a hydrogen atom, a C1 to C6 alkyl group which may be substituted with a halogen atom, a C2 to C6 alkenyl group which may be substituted with a halogen atom, a C2 to C6 alkynyl group which may be substituted with a halogen atom, a substituted or unsubstituted (C6 to C10) aryl group, or a substituted or unsubstituted 5- to 10-membered heterocycle], $R_5$ represents a C1 to C6 alkyl group which may be substituted with a halogen atom, a C2 to C6 alkenyl group which may be substituted with a halogen atom, a C2 to C6 alkynyl group which may be substituted with a halogen atom, a substituted or unsubstituted (C6 to C10) aryl group, a substituted or unsubstituted (C6 to C10) aryl (C1 to C6) alkyl group, a substituted or unsubstituted (C6 to C10) aryl (C2 to C6) alkenyl group, a substituted or unsubstituted (C6 to C10) aryl (C2 to C6) alkynyl group, a substituted or unsubstituted phenoxy (C1 to C6) alkyl group, a substituted or unsubstituted phenoxy (C2 to C6) alkenyl group, a substituted or unsubstituted phenoxy (C2 to C6) alkynyl group, a substituted or unsubstituted 5- to 10-membered heterocycle, a substituted or unsubstituted 5- to 10-membered heterocycle (C1 to C6) alkyl group, a substituted or unsubstituted 5- to 10-membered heterocycle (C2 to C6) alkenyl group, a substituted or unsubstituted 5- to 10-membered heterocycle (C2 to C6) alkynyl group, a (C1 to C4) alkoxy (C1 to C5) alkyl group, a (C1 to C4) alkoxy (C2 to C5) alkenyl group, a (C1 to C4) alkoxy (C2 to C5) alkynyl group, a (C1 to C4) alkylthio (C1 to C5) alkyl group, a (C1 to C4) alkylthio (C2 to C5) alkenyl group, or a (C1 to C4) alkylthio (C2 to C5) alkynyl group, $R_6$ represents a hydrogen atom, a formyl group, a O,O'—C1 to C4 alkyl phosphoryl group, a C1 to C18 alkyl group which may be substituted, a C2 to C6 alkenyl group which may be substituted with a halogen atom, a C2 to C6 alkynyl group which may be substituted with a halogen atom, a substituted or unsubstituted (C6 to C10) aryl group, a substituted or unsubstituted (C6 to C10) aryl (C1 to C6) alkyl group, a substituted or unsubstituted (C6 to C10) aryl (C2 to C6) alkenyl group, a substituted or unsubstituted (C6 to C10) aryl (C2 to C6) alkynyl group, a substituted or unsubstituted phenoxy (C1 to C6) alkyl group, a substituted or unsubstituted phenoxy (C2 to C6) alkenyl group, a substituted or unsubstituted phenoxy (C2 to C6) alkynyl group, a substituted or unsubstituted 5- to 10-membered heterocycle, a substituted or unsubstituted 5- to 10-membered heterocycle (C1 to C6) alkyl group, a substituted or unsubstituted 5- to 10-membered heterocycle (C2 to C6) alkenyl group, a substituted or unsubstituted 5- to 10-membered heterocycle (C2 to C6) alkynyl group, a (C1 to C4) alkoxy (C1 to C5) alkyl group, a (C1 to C4) alkoxy (C2 to C5) alkenyl group, a (C1 to C4) alkoxy (C2 to C5) alkynyl group, a (C1 to C4) alkylthio (C1 to C5) alkyl group, a (C1 to C4) alkylthio (C2 to C5) alkenyl group, a (C1 to C4) alkylthio (C2 to C5) alkynyl group, or a group represented by the following Formulae (o) to (x)

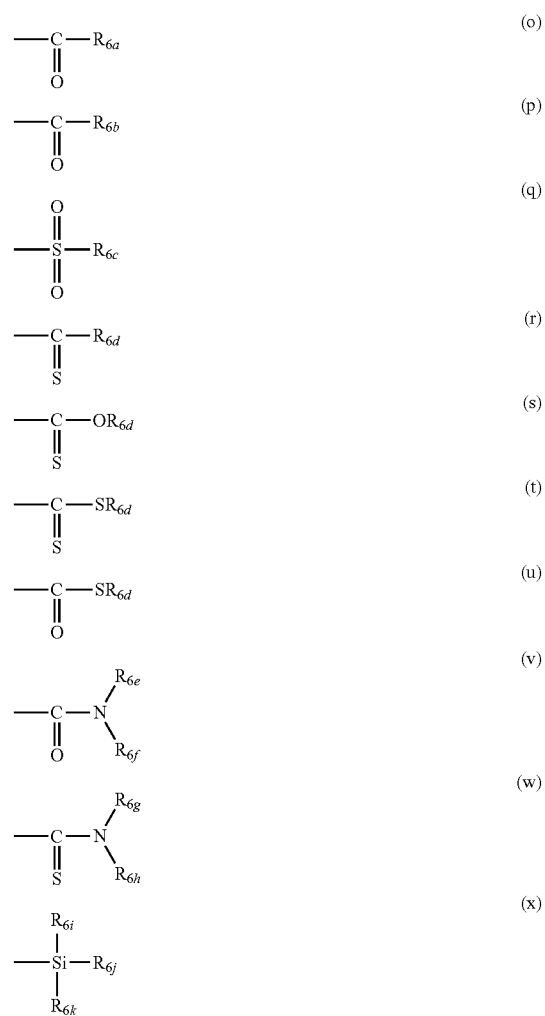

[here, $R_{6a}$, $R_{6b}$ and $R_{6c}$ represent a C1 to C6 alkyl group which may be substituted with a halogen atom, a C2 to C6 alkenyl group which may be substituted with a halogen atom, a C2 to C6 alkynyl group which may be substituted with a halogen atom, a substituted or unsubstituted (C6 to C10) aryl group, a substituted or unsubstituted (C6 to C10) aryl (C1 to C6) alkyl group, a substituted or unsubstituted (C6 to C10) aryl (C2 to C6) alkenyl group, a substituted or unsubstituted (C6 to C10) aryl (C2 to C6) alkynyl group, a substituted or unsubstituted phenoxy (C1 to C6) alkyl group, a substituted or unsubstituted phenoxy (C2 to C6) alkenyl group, a substituted or unsubstituted phenoxy (C2 to C6) alkynyl group, a substituted or unsubstituted 5- to 10-membered heterocycle, a substituted or unsubstituted 5- to 10-membered heterocycle (C1 to C6) alkyl group, a substituted or unsubstituted 5- to 10-membered heterocycle (C2 to C6) alkenyl group, a substituted or unsubstituted 5- to 10-membered heterocycle (C2 to C6) alkynyl group, a (C1 to C4) alkoxy (C1 to C5) alkyl group, a (C1 to C4) alkoxy (C2 to C5) alkenyl group, a (C1 to C4) alkoxy (C2 to C5) alkynyl group, a (C1 to C4) alkylthio (C1 to C5) alkyl group, a (C1 to C4) alkylthio (C2 to C5) alkenyl group, or a (C1 to C4) alkylthio (C2 to C5) alkynyl group, $R_{6d}$ represents a C1 to C6 alkyl group which may be substituted with a halogen atom, a C2 to C6 alkenyl group which may be substituted with a halogen atom, a C2 to C6 alkynyl group which may be substituted with a halogen atom, a substituted or unsubstituted (C6 to C10) aryl group, or a substituted or unsubstituted 5- to 10-membered heterocycle, $R_{6e}$ and $R_{6f}$ each independently represent a hydrogen atom, a C1 to C6 alkyl group which may be substituted with a halogen atom, a C2 to C6 alkenyl group which may be substituted with a halogen atom, a C2 to C6 alkynyl group which may be substituted with a halogen atom, a (C1 to C4) alkoxy (C1 to C5) alkyl group, a (C1 to C4) alkylthio (C1 to C5) alkyl group, a substituted or unsubstituted (C6 to C10) aryl group, a substituted or unsubstituted (C6 to C10) aryl (C1 to C6) alkyl group, or a substituted or unsubstituted 5- to 10-membered heterocycle, $R_{6g}$ and $R_{6h}$ each independently represent a hydrogen atom, a C1 to C6 alkyl group which may be substituted with a halogen atom, a C2 to C6 alkenyl group which may be substituted with a halogen atom, a C2 to C6 alkynyl group which may be substituted with a halogen atom, a substituted or unsubstituted (C6 to C10) aryl group, or a substituted or unsubstituted 5- to 10-membered heterocycle, and $R_{6i}$, $R_{6j}$ and $R_{6k}$ each independently represent a hydrogen atom, a C1 to C6 alkyl group which may be substituted with a halogen atom, a C2 to C6 alkenyl group which may be substituted with a halogen atom, a C2 to C6 alkynyl group which may be substituted with a halogen atom, or a substituted or unsubstituted (C6 to C10) aryl group], and $R_7$ represents a C1 to C6 alkyl group which may be substituted with a halogen atom, a C2 to C6 alkenyl group which may be substituted with a halogen atom, a C2 to C6 alkynyl group which may be substituted with a halogen atom, a substituted or unsubstituted (C6 to C10) aryl group, a substituted or unsubstituted (C6 to C10) aryl (C1 to C6) alkyl group, a substituted or unsubstituted (C6 to C10) aryl (C2 to C6) alkenyl group, a substituted or unsubstituted (C6 to C10) aryl (C2 to C6) alkynyl group, a substituted or unsubstituted phenoxy (C1 to C6) alkyl group, a substituted or unsubstituted phenoxy (C2 to C6) alkenyl group, a substituted or unsubstituted phenoxy (C2 to C6) alkynyl group, a substituted or unsubstituted 5- to 10-membered heterocycle, a substituted or unsubstituted 5- to 10-membered heterocycle (C1 to C6) alkyl group, a substituted or unsubstituted 5- to 10-membered heterocycle (C2 to C6) alkenyl group, a substituted or unsubstituted 5- to 10-membered heterocycle (C2 to C6) alkynyl group, a (C1 to C4) alkoxy (C1 to C5) alkyl group, a (C1 to C4) alkoxy (C2 to C5) alkenyl group, a (C1 to C4) alkoxy (C2 to C5) alkynyl group, a (C1 to C4) alkylthio (C1 to C5) alkyl group, a (C1 to C4) alkylthio (C2 to C5) alkenyl group, or a (C1 to C4) alkylthio (C2 to C5) alkynyl group, $Y_1$ and $Y_2$ represent an oxygen atom or a sulfur atom, and may be the same or different, and $R_y$ represents a C1 to C6 alkyl group which may be substituted with a halogen atom, a C2 to C6 alkenyl group which may be substituted with a halogen atom, a C2 to C6 alkynyl group which may be substituted with a halogen atom, a substituted or unsubstituted (C6 to C10) aryl group, a substituted or unsubstituted (C6 to C10) aryl (C1 to C6) alkyl group, a substituted or unsubstituted (C6 to C10) aryl (C2 to C6) alkenyl group, a substituted or unsubstituted (C6 to C10) aryl (C2 to C6) alkynyl group, a substituted or unsubstituted phenoxy (C1 to C6) alkyl group, a substituted or unsubstituted phenoxy (C2 to C6) alkenyl group, a substituted or unsubstituted phenoxy (C2 to C6) alkynyl group, a substituted or unsubstituted 5- to 10-membered heterocycle, a substituted or unsubstituted 5- to 10-membered heterocycle (C1 to C6) alkyl group, a substituted or unsubstituted 5- to 10-membered heterocycle (C2 to C6) alkenyl group, or a substituted or unsubstituted 5- to 10-membered heterocycle (C2 to C6) alkynyl group, $R_z$ represents a C1 to C6 alkyl group which may be substituted with a halogen atom, a C2 to C6 alkenyl group which may be substituted with a halogen atom, a C2 to C6 alkynyl group which may be substituted with a halogen atom, a substituted or unsubstituted (C6 to C10) aryl group, a substituted or unsubstituted (C6 to C10) aryl (C1 to C6) alkyl group, a substituted or unsubstituted (C6 to C10) aryl (C2 to C6) alkenyl group, a substituted or unsubstituted (C6 to C10) aryl (C2 to C6) alkynyl group, a substituted or unsubstituted phenoxy (C1 to C6) alkyl group, a substituted or unsubstituted phenoxy (C2 to C6) alkenyl group, a substituted or unsubstituted phenoxy (C2 to C6) alkynyl group, a substituted or unsubstituted 5- to 10-membered heterocycle, a substituted or unsubstituted 5- to 10-membered heterocycle (C1 to C6) alkyl group, a substituted or unsubstituted 5- to 10-membered heterocycle (C2 to C6) alkenyl group, a substituted or unsubstituted 5- to 10-membered heterocycle (C2 to C6) alkynyl group, a (C1 to C4) alkoxy (C1 to C5) alkyl group, a (C1 to C4) alkoxy (C2 to C5) alkenyl group, a (C1 to C4) alkoxy (C2 to C5) alkynyl group, a (C1 to C4) alkylthio (C1 to C5) alkyl group, a (C1 to C4) alkylthio (C2 to C5) alkenyl group, or a (C1 to C4) alkylthio (C2 to C5) alkynyl group, and n represents 1 or 2]

(2) The honeybee parasitic pest control agent according to (1), comprising:

at least one of an amine derivative represented by the following Formula (Ia) or acid addition salts thereof as the active ingredient.

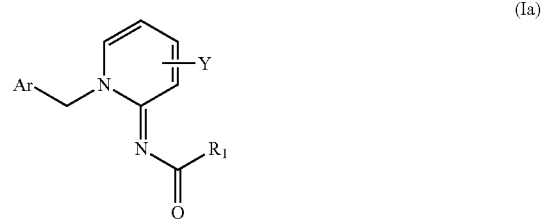

(Ia)

[here, Ar represents a pyridyl group which may be substituted with a halogen atom, a hydroxyl group, a C1 to C6 alkyl group which may be substituted with a halogen atom, a C1 to C6 alkyloxy group which may be substituted with a halogen atom, a cyano group, or a nitro group, or a pyrimidyl group which may be substituted with a halogen atom, a C1 to C4 alkyl group which may be substituted with a halogen atom, an alkyloxy group which may be substituted with a halogen atom, a hydroxyl group, a cyano group, or a nitro group, Y represents a hydrogen atom, a halogen atom, a hydroxyl group, a C1 to C6 alkyl group which may be substituted with a halogen atom, a C1 to C6 alkyloxy group which may be substituted with a halogen atom, a cyano group, or a nitro group, and $R_1$ represents a C1 to C6 alkyl group which is substituted with halogen]

(3) The honeybee parasitic pest control agent according to (1), comprising:

at least one of an amine derivative represented by the following Formula (Ic) or acid addition salts thereof as the active ingredient.

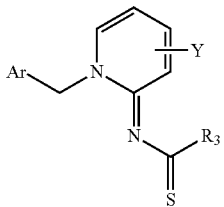

[here, Ar represents a pyridyl group which may be substituted with a halogen atom, a hydroxyl group, a C1 to C6 alkyl group which may be substituted with a halogen atom, a C1 to C6 alkyloxy group which may be substituted with a halogen atom, a cyano group, or a nitro group, or a pyrimidyl group which may be substituted with a halogen atom, a C1 to C4 alkyl group which may be substituted with a halogen atom, an alkyloxy group which may be substituted with a halogen atom, a hydroxyl group, a cyano group, or a nitro group, Y represents a hydrogen atom, a halogen atom, a hydroxyl group, a C1 to C6 alkyl group which may be substituted with a halogen atom, a C1 to C6 alkyloxy group which may be substituted with a halogen atom, a cyano group, or a nitro group, and $R_3$ represents a C1 to C6 alkyl group which may be substituted with halogen]

(4) The honeybee parasitic pest control agent according to (1), wherein ring A in Formula (I) represented by the following Formula:

is a ring with Formula (A-1):

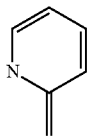

and Y is a hydrogen atom, a halogen atom and a cyano group.

(5) The honeybee parasitic pest control agent according to (1) or (4), wherein R in Formula (I) is a group with Formula (c):

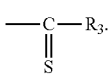

(6) The honeybee parasitic pest control agent according to (1) or (4), wherein R in Formula (I) is a group with Formula (a):

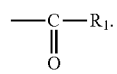

(7) The honeybee parasitic pest control agent according to (1) or (4), wherein R in Formula (I) is a group with Formula (d):

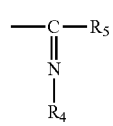

and $R_4$ represents a C1 to C18 alkyl group which may be substituted, a C2 to C6 alkenyl group which may be substituted with a halogen atom, a C2 to C6 alkynyl group which may be substituted with a halogen atom, a substituted or unsubstituted (C6 to C10) aryl group, a substituted or unsubstituted (C6 to C10) aryl (C1 to C6) alkyl group, a substituted or unsubstituted (C6 to C10) aryl (C2 to C6) alkenyl group, a substituted or unsubstituted (C6 to C10) aryl (C2 to C6) alkynyl group, a substituted or unsubstituted phenoxy (C1 to C6) alkyl group, a substituted or unsubstituted phenoxy (C2 to C6) alkenyl group, a substituted or unsubstituted phenoxy (C2 to C6) alkynyl group, a substituted or unsubstituted 5- to 10-membered heterocycle, a substituted or unsubstituted 5- to 10-membered heterocycle (C1 to C6) alkyl group, a substituted or unsubstituted 5- to 10-membered heterocycle (C2 to C6) alkenyl group, a substituted or unsubstituted 5- to 10-membered heterocycle (C2 to C6) alkynyl group, a (C1 to C4) alkoxy (C1 to C5) alkyl group, a (C1 to C4) alkoxy (C2 to C5) alkenyl group, a (C1 to C4) alkoxy (C2 to C5) alkynyl group, a (C1 to C4) alkylthio (C1 to C5) alkyl group, a (C1 to C4) alkylthio (C2 to C5) alkenyl group, a (C1 to C4) alkylthio (C2 to C5) alkynyl group, and $R_5$ is a C1 to C6 alkyl group which may be substituted with a halogen atom, a C2 to C6 alkenyl group which may be substituted with a halogen atom, a C2 to C6 alkynyl group which may be substituted with a halogen atom.

(8) The honeybee parasitic pest control agent according to any one of (1) to (7), wherein Ar is any one of a 6-chloro-3-pyridyl group, a 6-chloro-5-fluoro-3-pyridyl group, a 6-fluoro-3-pyridyl group, a 6-bromo-3-pyridyl group, and a 2-chloro-5-pyrimidyl group.

(9) A pest control method for honeybee parasitic pests, wherein the method uses the honeybee parasitic pest control agent according to any one of (1) to (8).

(10) The pest control method for honeybee parasitic pests according to (9), wherein the honeybee parasitic pests are any one of *Varroa* mites such as *Varroa destructor* and *Varroa jacobsoni*, honeybee *Tropilaelaps*, and *Acarapis woodi*.

(11) The pest control method for honeybee parasitic pests according to any one of (9) and (10), comprising spraying the honeybee parasitic pest control agent diluted with water or without dilution to a hive of honeybees such that the active ingredient is applied in an effective amount.

(12) The pest control method for honeybee parasitic pests according to any one of (9) and (10), comprising bringing honeybees into contact with a paper or tape material having been dipped into or coated with the honeybee parasitic pest control agent such that the active ingredient is applied in an effective amount.

(13) The pest control method for honeybee parasitic pests according to any one of (9) and (10), comprising mixing the honeybee parasitic pest control agent with water or a feed such that the active ingredient is applied in the effective amount.

(14) The pest control method for honeybee parasitic pests according to any one of (9) and (10), comprising subjecting a plant to any one of foliar treatment, seed treatment, nursery tray treatment, soil treatment, trunk injection, and trunk coating, using the honeybee parasitic pest control agent diluted with water or without dilution, such that the active ingredient is applied in the effective amount to thereby control the honeybee parasitic pests.

The honeybee parasitic pest control agent of the present invention is highly safe to honeybees and demonstrates excellent pest control effects against honeybee parasitic pests. Note that, in the present invention, the term "pest control" includes killing of honeybee parasitic pests, prevention of parasitism of honeybee parasitic pests in honeybees, and removal of honeybee parasitic pests parasitizing honeybees.

DETAILED DESCRIPTION OF THE PREFERRED EMBODIMENTS

A compound (iminopyridine derivative) represented by Formula (I) may be prepared by the following method when each type of substituent of R is indicated.

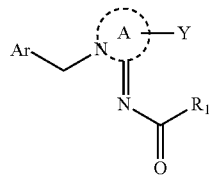

(I-1)

A compound represented by Formula (I-1) may be obtained by reacting a compound represented by the following Formula (II-1) with a compound represented by ArCH$_2$X [the definition of Ar, A, Y and R$_1$ has the same meaning as the definition described above, and X represents a halogen atom or OTs, OMs and the like] in the presence or absence of a base.

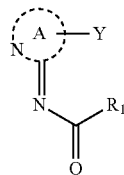

(II-1)

When the reaction is performed in the presence of a base, it is possible to use, for example, an alkali metal hydride such as sodium hydride; a carbonate such as potassium carbonate or sodium carbonate; an alkali metal hydroxide such as potassium hydroxide, and sodium hydroxide; tertiary amines such as triethylamine and 1,8-diazabicyclo[4.3.0]non-5-ene; and unsubstituted or substituent-containing pyridines, such as pyridine and 4-dimethylaminopyridine; as the base.

The reaction may be performed without a solvent or using a solvent which does not affect the reaction, and when a solvent is used, it is possible to use solvents such as, for example, amides such as N,N-dimethylformamide and N,N-dimethylacetamide; nitriles such as acetonitrile; sulfoxides such as dimethyl sulfoxide; ethers such as diethyl ether and tetrahydrofuran; esters such as ethyl acetate and butyl acetate; aromatic hydrocarbons such as benzene, xylene and toluene; alcohols such as methanol, ethanol, propanol and isopropyl alcohol; ketones such as acetone and methyl ethyl ketone; aliphatic hydrocarbons such as hexane, heptane and octane; and halogen hydrocarbons such as dichloromethane, chloroform, chlorobenzene and dichlorobenzene; either alone or in combination of two or more thereof, but N,N-dimethylformamide and the like are preferably used.

The reaction may be performed usually at 0° C. to 200° C., and it is preferred that reagents are added at 20° C. to 40° C. and the reaction is performed at 60° C. to 80° C.

The compound represented by Formula (II-1) may be obtained by reacting a compound represented by R$_1$—C(=O)X, R$_1$—C(=O)OC(=O)R$_1$, R$_1$C(=O)OR' [X represents a halogen atom or OTs, OMs and the like, R' represents a C1 to C6 alkyl group, and the definition of R$_1$, A and Y has the same meaning as the definition described above] and the like with a compound represented by the following Formula (III) in the presence or absence of a base.

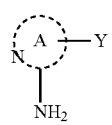

(III)

When the reaction is performed in the presence of a base, it is possible to use, for example, an alkali metal hydride such as sodium hydride; a carbonate such as potassium carbonate or sodium carbonate; an alkali metal hydroxide such as potassium hydroxide and sodium hydroxide; tertiary amines such as triethylamine and 1,8-diazabicyclo[4.3.0]non-5-ene; and unsubstituted or substituent-containing pyridines, such as pyridine and 4-dimethylaminopyridine; as the base.

The reaction may be performed without a solvent or using a solvent which does not affect the reaction. When a solvent is used, it is possible to use solvents such as, for example, amides such as N,N-dimethylformamide and N,N-dimethylacetamide; nitriles such as acetonitrile; sulfoxides such as dimethyl sulfoxide; ethers such as diethyl ether and tetrahydrofuran; esters such as ethyl acetate and butyl acetate; aromatic hydrocarbons such as benzene, xylene and toluene; alcohols such as methanol, ethanol and propanol; ketones such as acetone and methyl ethyl ketone; aliphatic hydrocarbons such as hexane, heptane and octane; halogen hydrocarbons such as dichloromethane, chloroform, chlorobenzene and dichlorobenzene; and water; either alone or in combination of two or more thereof, but toluene, N,N-dimethylformamide, acetonitrile, ethers, dichloromethane, chloroform and the like are preferably used.

The reaction may be performed usually at −80° C. to 100° C., and is performed preferably in a range from 20° C. to 50° C.

The compound represented by Formula (II-1) may be obtained by reacting the compound represented by Formula (III) with a carboxylic acid represented by R$_1$—COOH [the definition of R$_1$ has the same meaning as the definition described above] using a dehydration condensation agent in the presence or absence of a base, or may be obtained by performing the reaction using phosphorus pentaoxide, sulfuric acid, polyphosphoric acid, thionyl chloride, phosphorus oxychloride and oxalyl dichloride in the absence of a base.

It is possible to use a carbodiimide-based compound such as dicyclohexylcarbodiimide and 1-ethyl-3-(3-[dimethylaminopropyl])carbodiimide hydrochloride as the dehydration condensation agent.

When the reaction is performed in the presence of a base, it is possible to use, for example, a carbonate such as potassium carbonate or sodium carbonate; tertiary amines such as triethylamine and 1,8-diazabicyclo[4.3.0]non-5-ene; and unsubstituted or substituent-containing pyridines, such as pyridine and 4-dimethylaminopyridine; as the base.

The reaction is preferably performed by using a solvent, and it is possible to use solvents such as, for example, amides such as N,N-dimethylformamide and N,N-dimethylacetamide; nitriles such as acetonitrile; sulfoxides such as dimethyl sulfoxide; ethers such as diethyl ether and tetrahydrofuran; esters such as ethyl acetate and butyl acetate; aromatic hydrocarbons such as benzene, xylene and toluene; ketones such as acetone and methyl ethyl ketone; aliphatic hydrocarbons such as hexane, heptane and octane; and halogen hydrocarbons such as dichloromethane, chloroform, chlorobenzene and dichlorobenzene; either alone or in combination of two or more thereof, but dichloromethane, chloroform and the like are preferably used.

The reaction may be performed usually at −80° C. to 100° C., and is performed preferably in a range from 20° C. to 50° C.

The compound represented by Formula (I-1) may be obtained by reacting a compound represented by $R_1$—C(=O)X, $R_1$—C(=O)OC(=O)$R_1$, $R_1$C(=O)OR' [X represents a halogen atom or OTs, OMs and the like, R' represents a C1 to C6 alkyl group, and the definition of Ar, A, Y and $R_1$ has the same meaning as the definition described above] and the like with a compound represented by the following Formula (IV) in the presence or absence of a base.

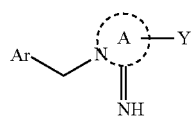

(IV)

When the reaction is performed in the presence of a base, it is possible to use, for example, an alkali metal hydride such as sodium hydride; a carbonate such as potassium carbonate or sodium carbonate; an alkali metal hydroxide such as potassium hydroxide and sodium hydroxide; tertiary amines such as triethylamine and 1,8-diazabicyclo[4.3.0]non-5-ene; and unsubstituted or substituent-containing pyridines, such as pyridine and 4-dimethylaminopyridine; as the base.

The reaction may be performed without a solvent or using a solvent which does not affect the reaction. When a solvent is used, it is possible to use solvents such as, for example, amides such as N,N-dimethylformamide and N,N-dimethylacetamide; nitriles such as acetonitrile; sulfoxides such as dimethyl sulfoxide; ethers such as diethyl ether and tetrahydrofuran; esters such as ethyl acetate and butyl acetate; aromatic hydrocarbons such as benzene, xylene and toluene; alcohols such as methanol, ethanol and propanol; ketones such as acetone and methyl ethyl ketone; aliphatic hydrocarbons such as hexane, heptane and octane; halogen hydrocarbons such as dichloromethane, chloroform, chlorobenzene and dichlorobenzene; and water; either alone or in combination of two or more thereof, but toluene, N,N-dimethylformamide, acetonitrile, ethers, dichloromethane, chloroform and the like are preferably used.

The reaction may be performed usually at −80° C. to 100° C., and is performed preferably in a range from 20° C. to 50° C.

The compound represented by Formula (I-1) may be obtained by reacting the above-described compound represented by Formula (IV) with a carboxylic acid represented by $R_1$—COOH [the definition of $R_1$ has the same meaning as the definition described above] using a dehydration condensation agent in the presence or absence of a base, or may be obtained by performing the reaction using phosphorus pentaoxide, sulfuric acid, polyphosphoric acid, thionyl chloride, phosphorus oxychloride and oxalyl dichloride in the absence of a base.

It is possible to use a carbodiimide-based compound such as dicyclohexylcarbodiimide and 1-ethyl-3-(3-dimethylaminopropyl)carbodiimide hydrochloride as the dehydration condensation agent.

When the reaction is performed in the presence of a base, it is possible to use, for example, a carbonate such as potassium carbonate or sodium carbonate; tertiary amines such as triethylamine and 1,8-diazabicyclo[4.3.0]non-5-ene; and unsubstituted or substituent-containing pyridines, such as pyridine and 4-dimethylaminopyridine; as the base.

The reaction is preferably performed by using a solvent, and it is possible to use solvents such as, for example, amides such as N,N-dimethylformamide and N,N-dimethylacetamide; nitriles such as acetonitrile; sulfoxides such as dimethyl sulfoxide; ethers such as diethyl ether and tetrahydrofuran; esters such as ethyl acetate and butyl acetate; aromatic hydrocarbons such as benzene, xylene and toluene; ketones such as acetone and methyl ethyl ketone; aliphatic hydrocarbons such as hexane, heptane and octane; and halogen hydrocarbons such as dichloromethane, chloroform, chlorobenzene and dichlorobenzene; either alone or in combination of two or more thereof, but dichloromethane, chloroform and the like are preferably used.

The reaction may be performed usually at −80° C. to 100° C., and is performed preferably in a range from 20° C. to 50° C.

The compound represented by Formula (IV) may be obtained by reacting the above-described compound represented by Formula (III) with a compound represented by ArCH$_2$X [the definition of Ar and X has the same meaning as the definition described above] in the presence or absence of a base.

When the reaction is performed in the presence of a base, it is possible to use, for example, an alkali metal hydride such as sodium hydride; a carbonate such as potassium carbonate or sodium carbonate; an alkali metal hydroxide such as potassium hydroxide and sodium hydroxide; tertiary amines such as triethylamine and 1,8-diazabicyclo[4.3.0]non-5-ene; and unsubstituted or substituent-containing pyridines, such as pyridine and 4-dimethylaminopyridine; as the base.

The reaction may be performed without a solvent or using a solvent which does not affect the reaction. When a solvent is used, it is possible to use solvents such as, for example, amides such as N,N-dimethylformamide and N,N-dimethylacetamide; nitriles such as acetonitrile; sulfoxides such as dimethyl sulfoxide; ethers such as diethyl ether and tetrahydrofuran; esters such as ethyl acetate and butyl acetate; aromatic hydrocarbons such as benzene, xylene and toluene; alcohols such as methanol, ethanol and propanol; ketones such as acetone and methyl ethyl ketone; aliphatic hydrocarbons such as hexane, heptane and octane; halogen hydrocarbons such as dichloromethane, chloroform, chlorobenzene and dichlorobenzene; and water; either alone or in combination of two or more thereof, but N,N-dimethylformamide, acetonitrile, ethers, dichloromethane, chloroform and the like are preferably used.

The reaction may be performed usually at −80° C. to 100° C., and is performed preferably in a range from 20° C. to 80° C.

When Formula (I-1) is synthesized via Formula (II-1) from the compound represented by Formula (III), or when Formula (I-1) is synthesized via Formula (IV) from the compound represented by Formula (III), the reaction may be continuously performed without taking out Formula (II-1) or Formula (IV), or the reactions from Formula (III) to Formula (I-1) may be simultaneously performed in the same vessel.

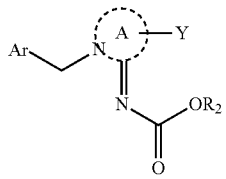

(I-2)

The compound represented by Formula (I-2) may be obtained by reacting a compound represented by the following Formula (I-2a) with a compound represented by $ArCH_2X$ [the definition of Ar, A, Y and $R_2$ has the same meaning as the definition described above, and X represents a halogen atom or OTs, OMs and the like] in the presence or absence of a base.

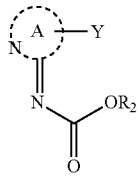

(I-2a)

When the reaction is performed in the presence of a base, it is possible to use, for example, an alkali metal hydride such as sodium hydride; a carbonate such as potassium carbonate or sodium carbonate; an alkali metal hydroxide such as potassium hydroxide and sodium hydroxide; tertiary amines such as triethylamine and 1,8-diazabicyclo[4.3.0]non-5-ene; and unsubstituted or substituent-containing pyridines, such as pyridine and 4-dimethylaminopyridine; as the base.

The reaction may be performed without a solvent or using a solvent which does not affect the reaction, and when a solvent is used, it is possible to use solvents such as, for example, amides such as N,N-dimethylformamide and N,N-dimethylacetamide; nitriles such as acetonitrile; sulfoxides such as dimethyl sulfoxide; ethers such as diethyl ether and tetrahydrofuran; esters such as ethyl acetate and butyl acetate; aromatic hydrocarbons such as benzene, xylene and toluene; alcohols such as methanol, ethanol, propanol and isopropyl alcohol; ketones such as acetone and methyl ethyl ketone; aliphatic hydrocarbons such as hexane, heptane and octane; and halogen hydrocarbons such as dichloromethane, chloroform, chlorobenzene and dichlorobenzene; either alone or in combination of two or more thereof, but N,N-dimethylformamide and the like are preferably used.

The reaction may be performed usually at 0° C. to 200° C., and it is preferred that reagents are added at 20° C. to 40° C. and the reaction is performed at 60° C. to 80° C.

The compound represented by Formula (I-2a) may be obtained by reacting the above-described compound represented by Formula (III) with a compound represented by $R_2OC(=O)X$ (the definition of $R_2$ and X has the same meaning as the definition described above] or represented by the following Formula (I-2b) in the presence or absence of a base.

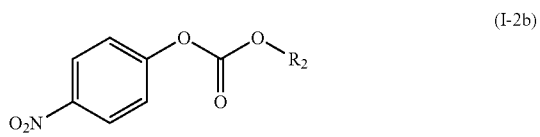

(I-2b)

When the reaction is performed in the presence of a base, it is possible to use, for example, an alkali metal hydride such as sodium hydride; a carbonate such as potassium carbonate or sodium carbonate; an alkali metal hydroxide such as potassium hydroxide and sodium hydroxide; tertiary amines such as triethylamine and 1,8-diazabicyclo[4.3.0]non-5-ene; and unsubstituted or substituent-containing pyridines, such as pyridine and 4-dimethylaminopyridine; as the base.

The reaction may be performed without a solvent or using a solvent which does not affect the reaction, and when a solvent is used, it is possible to use solvents such as, for example, amides such as N,N-dimethylformamide and N,N-dimethylacetamide; nitriles such as acetonitrile; sulfoxides such as dimethyl sulfoxide; ethers such as diethyl ether, and tetrahydrofuran; esters such as ethyl acetate and butyl acetate; aromatic hydrocarbons such as benzene, xylene and toluene; alcohols such as methanol, ethanol, propanol and isopropyl alcohol; ketones such as acetone and methyl ethyl ketone; aliphatic hydrocarbons such as hexane, heptane and octane; and halogen hydrocarbons such as dichloromethane, chloroform, chlorobenzene and dichlorobenzene; either alone or in combination of two or more thereof, but acetonitrile, dichloromethane or the like is preferably used.

The reaction may be performed usually at 0° C. to 200° C., and is performed preferably at 20° C. to 80° C.

The compound represented by Formula (I-2) may be obtained by reacting the above-described compound represented by Formula (IV) with a compound represented by $R_2OC(=O)X$ [the definition of $R_2$ and X has the same meaning as the definition described above] or represented by the above-described Formula (I-2b) in the presence or absence of a base.

When the reaction is performed in the presence of a base, it is possible to use, for example, an alkali metal hydride such as sodium hydride; a carbonate such as potassium carbonate or sodium carbonate; an alkali metal hydroxide such as potassium hydroxide and sodium hydroxide; tertiary amines such as triethylamine and 1,8-diazabicyclo[4.3.0]non-5-ene; and unsubstituted or substituent-containing pyridines, such as pyridine and 4-dimethylaminopyridine; as the base.

The reaction may be performed without a solvent or using a solvent which does not affect the reaction, and when a solvent is used, it is possible to use solvents such as, for example, amides such as N,N-dimethylformamide and N,N-dimethylacetamide; nitriles such as acetonitrile; sulfoxides such as dimethyl sulfoxide; ethers such as diethyl ether and tetrahydrofuran; esters such as ethyl acetate and butyl acetate; aromatic hydrocarbons such as benzene, xylene and toluene; alcohols such as methanol, ethanol, propanol and isopropyl alcohol; ketones such as acetone and methyl ethyl ketone; aliphatic hydrocarbons such as hexane, heptane and octane; and halogen hydrocarbons such as dichloromethane, chloroform, chlorobenzene and dichlorobenzene; either alone or in combination of two or more thereof, but acetonitrile, dichloromethane or the like is preferably used.

The reaction may be performed usually at 0° C. to 200° C., and is performed preferably at 20° C. to 80° C.

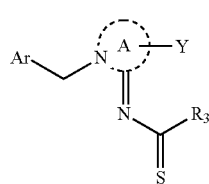

(I-3)

The compound represented by Formula (I-3) may be synthesized by acting a sulfurizing reagent on a compound [the definition of Ar, A, Y and R₃ has the same meaning as the definition described above] represented by the following Formula (II-3a), which may be synthesized in the same manner as described in Formula (I-1), in the presence or absence of a base.

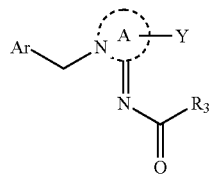

(II-3a)

When the reaction is performed in the presence of a base, it is possible to use, for example, an alkali metal hydride such as sodium hydride; a carbonate such as potassium carbonate or sodium carbonate; an alkali metal hydroxide such as potassium hydroxide and sodium hydroxide; tertiary amines such as triethylamine and 1,8-diazabicyclo[4.3.0]non-5-ene; and unsubstituted or substituent-containing pyridines, such as pyridine and 4-dimethylaminopyridine; as the base, but potassium carbonate, sodium carbonate or the like is preferably used.

As the sulfurizing reagent, phosphorus pentasulfide, Lawesson's reagent, hydrogen sulfide and the like may be used.

The reaction may be performed without a solvent or using a solvent which does not affect the reaction, and when a solvent is used, it is possible to use solvents such as, for example, amides such as N,N-dimethylformamide and N,N-dimethylacetamide; nitriles such as acetonitrile; sulfoxides such as dimethyl sulfoxide; ethers such as diethyl ether and tetrahydrofuran; esters such as ethyl acetate and butyl acetate; aromatic hydrocarbons such as benzene, xylene and toluene; alcohols such as methanol, ethanol and propanol; ketones such as acetone and methyl ethyl ketone; aliphatic hydrocarbons such as hexane, heptane and octane; and halogen hydrocarbons such as dichloromethane, chloroform, chlorobenzene and dichlorobenzene; either alone or in combination of two or more thereof, but toluene, tetrahydrofuran or the like is preferably used.

The reaction may be performed usually at −80° C. to 100° C., and is performed preferably in a range from 20° C. to 80° C.

The compound represented by Formula (I-3) may be obtained by reacting a compound represented by the following Formula (II-3b) with a compound represented by ArCH₂X [the definition of Ar, A, Y and R₃ has the same meaning as the definition described above, and X represents a halogen atom or OTs, OMs and the like] in the presence or absence of a base.

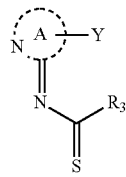

(II-3b)

When the reaction is performed in the presence of a base, it is possible to use, for example, an alkali metal hydride such as sodium hydride; a carbonate such as potassium carbonate or sodium carbonate; an alkali metal hydroxide such as potassium hydroxide and sodium hydroxide; tertiary amines such as triethylamine and 1,8-diazabicyclo[4.3.0]non-5-ene; and unsubstituted or substituent-containing pyridines, such as pyridine and 4-dimethylaminopyridine; as the base.

The reaction may be performed without a solvent or using a solvent which does not affect the reaction, and when a solvent is used, it is possible to use solvents such as, for example, amides such as N,N-dimethylformamide and N,N-dimethylacetamide; nitriles such as acetonitrile; sulfoxides such as dimethyl sulfoxide; ethers such as diethyl ether and tetrahydrofuran; esters such as ethyl acetate and butyl acetate; aromatic hydrocarbons such as benzene, xylene and toluene; alcohols such as methanol, ethanol, propanol and isopropyl alcohol; ketones such as acetone and methyl ethyl ketone; aliphatic hydrocarbons such as hexane, heptane and octane; and halogen hydrocarbons such as dichloromethane, chloroform, chlorobenzene and dichlorobenzene; either alone or in combination of two or more thereof, but N,N-dimethylformamide and the like are preferably used.

The reaction may be performed usually at 0° C. to 200° C., and it is preferred that reagents are added at 20° C. to 40° C. and the reaction is performed at 60° C. to 80° C.

The compound represented by Formula (II-3b) may be synthesized by acting a sulfurizing reagent on a compound [the definition of A, Y and R₃ has the same meaning as the definition described above] represented by Formula (II-3c), which may be synthesized in the same manner as described in Formula (II-1), in the presence or absence of a base.

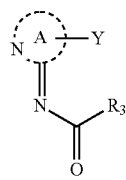

(II-3c)

When the reaction is performed in the presence of a base, it is possible to use, for example, an alkali metal hydride such as sodium hydride; a carbonate such as potassium carbonate or sodium carbonate; an alkali metal hydroxide such as potassium hydroxide and sodium hydroxide; tertiary amines such as triethylamine and 1,8-diazabicyclo[4.3.0]non-5-ene; and unsubstituted or substituent-containing pyridines, such as pyridine and 4-dimethylaminopyridine; as the base, but potassium carbonate, sodium carbonate or the like is preferably used.

As the sulfurizing reagent, phosphorus pentasulfide, Lawesson's reagent, hydrogen sulfide and the like may be used. The reaction may be performed without a solvent or using a solvent which does not affect the reaction, and when a solvent is used, it is possible to use solvents such as, for example, amides such as N,N-dimethylformamide and N,N-dimethylacetamide; nitriles such as acetonitrile; sulfoxides such as dimethyl sulfoxide; ethers such as diethyl ether and tetrahydrofuran; esters such as ethyl acetate and butyl acetate; aromatic hydrocarbons such as benzene, xylene and toluene; alcohols such as methanol, ethanol and propanol; ketones such as acetone and methyl ethyl ketone; aliphatic hydrocarbons such as hexane, heptane and octane; and halogen hydrocarbons such as dichloromethane, chloroform, chlorobenzene and dichlorobenzene; either alone or in combination of two or more thereof, but toluene, tetrahydrofuran and the like are preferably used.

The reaction may be performed usually at −80° C. to 100° C., and is performed preferably in a range from 20° C. to 80° C.

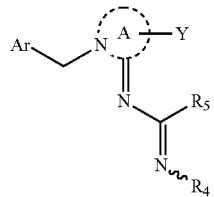

(I-4)

The compound represented by Formula (I-4) may be obtained by reacting a compound represented by the following Formula (II-4a), which may be synthesized in the same manner as described in Formula (I-3) with a compound represented by $R_4$—$NH_2$ [the definition of Ar, A, Y, $R_4$ and $R_5$ has the same meaning as the definition described above].

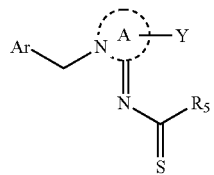

(II-4a)

The reaction may be performed without a solvent or using a solvent which does not affect the reaction, and when a solvent is used, it is possible to use solvents such as, for example, amides such as N,N-dimethylformamide and N,N-dimethylacetamide; nitriles such as acetonitrile; sulfoxides such as dimethyl sulfoxide; ethers such as diethyl ether and tetrahydrofuran; esters such as ethyl acetate and butyl acetate; aromatic hydrocarbons such as benzene, xylene and toluene; alcohols such as methanol, ethanol and propanol; ketones such as acetone and methyl ethyl ketone; aliphatic hydrocarbons such as hexane, heptane and octane; and halogen hydrocarbons such as dichloromethane, chloroform, chlorobenzene and dichlorobenzene; either alone or in combination of two or more thereof, but alcohols such as methanol and ethanol are preferably used.

The reaction, if performed in the presence of silver carbonate, copper carbonate and the like, progresses quickly, but may proceed without the compound.

The reaction may be performed usually at −80° C. to 100° C., and is performed preferably in a range from 20° C. to 80° C.

The compound represented by Formula (I-4) may be obtained by reacting a compound represented by the following Formula (I-4b) or a salt thereof with $R_4$—X, $R_4$—O—$R_4$ and $R_4$—OR' [the definition of $R_4$, R', Ar, A, Y and $R_5$ has the same meaning as the definition described above, and X represents a halogen atom] in the presence or absence of a base.

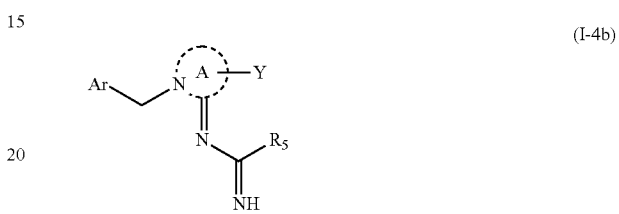

(I-4b)

When the reaction is performed in the presence of a base, it is possible to use, for example, an alkali metal hydride such as sodium hydride; a carbonate such as potassium carbonate or sodium carbonate; an alkali metal hydroxide such as potassium hydroxide and sodium hydroxide; tertiary amines such as triethylamine and 1,8-diazabicyclo[4.3.0]non-5-ene; and unsubstituted or substituent-containing pyridines, such as pyridine and 4-dimethylaminopyridine; as the base.

The reaction may be performed without a solvent or using a solvent which does not affect the reaction. When a solvent is used, it is possible to use solvents such as, for example, amides such as N,N-dimethylformamide and N,N-dimethylacetamide; nitriles such as acetonitrile; sulfoxides such as dimethyl sulfoxide; ethers such as diethyl ether and tetrahydrofuran; esters such as ethyl acetate and butyl acetate; aromatic hydrocarbons such as benzene, xylene and toluene; alcohols such as methanol, ethanol and propanol; ketones such as acetone and methyl ethyl ketone; aliphatic hydrocarbons such as hexane, heptane and octane; halogen hydrocarbons such as dichloromethane, chloroform, chlorobenzene and dichlorobenzene; and water; either alone or in combination of two or more thereof, but toluene, dimethylformamide, acetonitrile, ethers, dichloromethane, chloroform and the like are preferably used.

The reaction may be performed usually at −80° C. to 100° C., and is performed preferably in a range from 20° C. to 50° C.

The compound represented by Formula (I-4b) may be obtained by reacting a compound represented by Formula (II-4a) with ammonia or an alcohol solution thereof, ammonium chloride and the like.

The reaction may be performed without a solvent or using a solvent which does not affect the reaction. When a solvent is used, it is possible to use solvents such as, for example, amides such as N,N-dimethylformamide and N,N-dimethylacetamide; nitriles such as acetonitrile; sulfoxides such as dimethyl sulfoxide; ethers such as diethyl ether and tetrahydrofuran; esters such as ethyl acetate and butyl acetate; aromatic hydrocarbons such as benzene, xylene and toluene; alcohols such as methanol, ethanol and propanol; ketones such as acetone and methyl ethyl ketone; aliphatic hydrocarbons such as hexane, heptane and octane; halogen hydrocarbons such as dichloromethane, chloroform, chlorobenzene and dichlorobenzene; and water; either alone or in combination of two or more thereof, but alcohols such as methanol and ethanol are preferably used.

The reaction may be performed usually at −80° C. to 100° C., and is performed preferably in a range from 20° C. to 50° C.

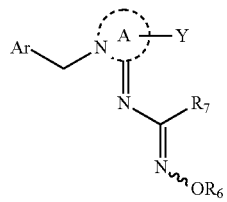

(I-5)

The compound represented by Formula (I-5) may be obtained by reacting a compound represented by the following Formula (II-5b) with $R_6$—X [the definition of AR, A, Y, $R_6$ and $R_7$ has the same meaning as the definition described above, and X represents a halogen atom], $R_6$—O—$R_6$ or $R_6$—OR' [the definition of R' has the same meaning as the definition described above] in the presence or absence of a base.

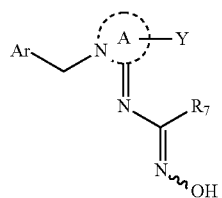

(II-5b)

When the reaction is performed in the presence of a base, it is possible to use, for example, an alkali metal hydride such as sodium hydride; a carbonate such as potassium carbonate or sodium carbonate; an alkali metal hydroxide such as potassium hydroxide and sodium hydroxide; tertiary amines such as triethylamine and 1,8-diazabicyclo[4.3.0]non-5-ene; and unsubstituted or substituent-containing pyridines, such as pyridine and 4-dimethylaminopyridine; as the base.

The reaction may be performed without a solvent or using a solvent which does not affect the reaction. When a solvent is used, it is possible to use solvents such as, for example, amides such as N,N-dimethylformamide and N,N-dimethylacetamide; nitriles such as acetonitrile; sulfoxides such as dimethyl sulfoxide; ethers such as diethyl ether and tetrahydrofuran; esters such as ethyl acetate and butyl acetate; aromatic hydrocarbons such as benzene, xylene and toluene; alcohols such as methanol, ethanol and propanol; ketones such as acetone and methyl ethyl ketone; aliphatic hydrocarbons such as hexane, heptane and octane; halogen hydrocarbons such as dichloromethane, chloroform, chlorobenzene and dichlorobenzene; and water; either alone or in combination of two or more thereof, but toluene, N,N-dimethylformamide, acetonitrile, ethers, dichloromethane and chloroform are preferably used.

The reaction may be performed usually at −80° C. to 100° C., and is performed preferably in a range from 20° C. to 50° C.

When $R_6$ represents —C(=O)$R_{6a}$ [$R_{6a}$ has the same meaning as described above], the compound represented by Formula (I-5) may be obtained by reacting the compound represented by Formula (II-5b) with a carboxylic acid represented by $R_{6a}$—C(=O)OH [the definition of $R_{6a}$ has the same meaning as the definition described above] using a dehydration condensation agent in the presence or absence of a base, or may be obtained by performing the reaction using phosphorus pentaoxide, sulfuric acid, polyphosphoric acid, thionyl chloride, phosphorus oxychloride and oxalyl dichloride in the absence of a base.

It is possible to use a carbodiimide-based compound such as dicyclohexylcarbodiimide, 1-ethyl-3-(3-dimethylaminopropyl)carbodiimide hydrochloride and the like as the dehydration condensation agent.

When the reaction is performed in the presence of a base, it is possible to use, for example, a carbonate such as potassium carbonate or sodium carbonate; tertiary amines such as triethylamine and 1,8-diazabicyclo[4.3.0]non-5-ene; and unsubstituted or substituent-containing pyridines, such as pyridine and 4-dimethylaminopyridine; as the base.

The reaction is preferably performed by using a solvent, and it is possible to use, for example, amides such as N,N-dimethylformamide and N,N-dimethylacetamide; nitriles such as acetonitrile; sulfoxides such as dimethyl sulfoxide; ethers such as diethyl ether and tetrahydrofuran; esters such as ethyl acetate and butyl acetate; aromatic hydrocarbons such as benzene, xylene and toluene; ketones such as acetone and methyl ethyl ketone; aliphatic hydrocarbons such as hexane, heptane and octane; and halogen hydrocarbons such as dichloromethane, chloroform, chlorobenzene and dichlorobenzene; either alone or in combination of two or more thereof, but dichloromethane, chloroform and the like are preferably used.

The reaction may be performed usually at −80° C. to 100° C., and is performed preferably in a range from 20° C. to 50° C.

When $R_6$ represents —CONR$_{6e}$R$_{6f}$ [the definition of $R_{6e}$ and $R_{6f}$ has the same meaning as the definition described above, and $R_{6e}$ or $R_{6f}$ represents a hydrogen atom] or —CSNR$_{6g}$R$_{6h}$ [the definition of $R_{6g}$ and $R_{6h}$ has the same meaning as the definition described above, and $R_{6g}$ or $R_{6h}$ represents a hydrogen atom], the compound of Formula (I-5) may be obtained by reacting the Formula (II-5b) with a compound represented by R"N=C=O [R" represents a C1 to C6 alkyl group which may be substituted with a halogen atom, a C2 to C6 alkenyl group which may be substituted with a halogen atom, a C2 to C6 alkynyl group which may be substituted with a halogen atom, a (C1 to C4) alkoxy (C1 to C5) alkyl group, a (C1 to C4) alkylthio (C1 to C5) alkyl group, a substituted or unsubstituted (C6 to C10) aryl group, and a substituted or unsubstituted 5- to 10-membered heterocycle] in the presence or absence of a base.

When the reaction is performed in the presence of a base, it is possible to use, for example, an alkali metal hydride such as sodium hydride; a carbonate such as potassium carbonate or sodium carbonate; an alkali metal hydroxide such as potassium hydroxide and sodium hydroxide; tertiary amines such as triethylamine and 1,8-diazabicyclo[4.3.0]non-5-ene; and unsubstituted or substituent-containing pyridines, such as pyridine and 4-dimethylaminopyridine; as the base.

The reaction is preferably performed by using a solvent, and it is possible to use, for example, amides such as N,N-dimethylformamide and N,N-dimethylacetamide; nitriles such as acetonitrile; sulfoxides such as dimethyl sulfoxide; ethers such as diethyl ether and tetrahydrofuran; esters such as ethyl acetate and butyl acetate; aromatic hydrocarbons such as benzene, xylene and toluene; ketones such as acetone and methyl ethyl ketone; aliphatic hydrocarbons such as hexane; heptane and octane, and halogen hydrocarbons such as dichloromethane, chloroform, chlorobenzene and dichlorobenzene; either alone or in combination of two or more thereof, but nitriles such as acetonitrile are preferably used.

The reaction may be performed usually at −80° C. to 100° C., and is performed preferably in a range from 20° C. to 80° C.

When $R_6$ represents —$CONR_{6e}R_{6f}$ [the definition of $R_{6e}$ and $R_{6f}$ has the same meaning as the definition described above], the compound of Formula (I-5) may be obtained by reacting the above-described compound represented by Formula (II-5b) with a compound represented by the following Formula (II-5c) in the presence or absence of a base.

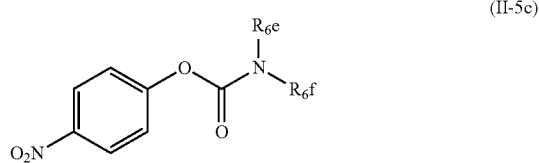

(II-5c)

When the reaction is performed in the presence of a base, it is possible to use, for example, an alkali metal hydride such as sodium hydride; a carbonate such as potassium carbonate or sodium carbonate; an alkali metal hydroxide such as potassium hydroxide and sodium hydroxide; tertiary amines such as triethylamine and 1,8-diazabicyclo[4.3.0]non-5-ene; and unsubstituted or substituent-containing pyridines, such as pyridine and 4-dimethylaminopyridine; as the base.

The reaction is preferably performed by using a solvent, and it is possible to use, for example, amides such as N,N-dimethylformamide and N,N-dimethylacetamide; nitriles such as acetonitrile; sulfoxides such as dimethyl sulfoxide; ethers such as diethyl ether and tetrahydrofuran; esters such as ethyl acetate and butyl acetate; aromatic hydrocarbons such as benzene, xylene and toluene; ketones such as acetone and methyl ethyl ketone; aliphatic hydrocarbons such as hexane, heptane and octane; and halogen hydrocarbons such as dichloromethane, chloroform, chlorobenzene and dichlorobenzene; either alone or in combination of two or more thereof, but nitriles such as acetonitrile are preferably used.

The reaction may be performed usually at −80° C. to 100° C., and is performed preferably in a range from 20° C. to 80° C.

The compound represented by Formula (II-5b) may be obtained by reacting the compound [the definition of Ar, A, Y and $R_7$ has the same meaning as the definition described above] represented by Formula (II-5a), which may be synthesized in the same manner as described in Formula (I-3) with hydroxylamine or a salt thereof in the presence or absence of a base.

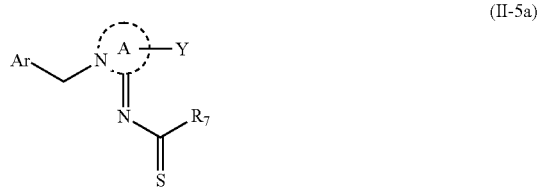

(II-5a)

When the reaction is performed in the presence of a base, it is possible to use, for example, an alkali metal hydride such as sodium hydride; a carbonate such as potassium carbonate or sodium carbonate; an alkali metal hydroxide such as potassium hydroxide and sodium hydroxide; tertiary amines such as triethylamine and 1,8-diazabicyclo[4.3.0]non-5-ene; and unsubstituted or substituent-containing pyridines, such as pyridine and 4-dimethylaminopyridine; as the base.

The reaction may be performed without a solvent or using a solvent which does not affect the reaction. When a solvent is used, it is possible to use solvents such as, for example, amides such as N,N-dimethylformamide and N,N-dimethylacetamide; nitriles such as acetonitrile; sulfoxides such as dimethyl sulfoxide; ethers such as diethyl ether and tetrahydrofuran; esters such as ethyl acetate and butyl acetate; aromatic hydrocarbons such as benzene, xylene and toluene; alcohols such as methanol, ethanol and propanol; ketones such as acetone and methyl ethyl ketone; aliphatic hydrocarbons such as hexane, heptane and octane; halogen hydrocarbons such as dichloromethane, chloroform, chlorobenzene and dichlorobenzene; and water; either alone or in combination of two or more thereof, but toluene, N,N-dimethylformamide, acetonitrile, ethers, dichloromethane, chloroform and the like are preferably used.

The reaction may be performed usually at −80° C. to 100° C., and is performed preferably in a range from 20° C. to 80° C.

The compound represented by Formula (I-5) may also be obtained by reacting the compound represented by Formula (II-5a) with a compound represented by $R_6$—$ONH_2$ or a salt thereof in the presence or absence of a base.

When the reaction is performed in the presence of a base, it is possible to use, for example, an alkali metal hydride such as sodium hydride; a carbonate such as potassium carbonate or sodium carbonate; an alkali metal hydroxide such as potassium hydroxide and sodium hydroxide; tertiary amines such as triethylamine and 1,8-diazabicyclo[4.3.0]non-5-ene; and unsubstituted or substituent-containing pyridines, such as pyridine and 4-dimethylaminopyridine; as the base.

The reaction may be performed without a solvent or using a solvent which does not affect the reaction. When a solvent is used, it is possible to use solvents such as, for example, amides such as N,N-dimethylformamide and N,N-dimethylacetamide; nitriles such as acetonitrile; sulfoxides such as dimethyl sulfoxide; ethers such as diethyl ether and tetrahydrofuran; esters such as ethyl acetate and butyl acetate; aromatic hydrocarbons such as benzene, xylene and toluene; alcohols such as methanol, ethanol and propanol; ketones such as acetone and methyl ethyl ketone; aliphatic hydrocarbons such as hexane, heptane and octane; halogen hydrocarbons such as dichloromethane, chloroform, chlorobenzene and dichlorobenzene; and water; either alone or in combination of two or more thereof, but alcohols such as methanol and ethanol are preferably used.

The reaction may be performed usually at −80° C. to 100° C., and is performed preferably in a range from 20° C. to 80° C.

The reaction, if performed in the presence of silver carbonate, copper carbonate and the like, progresses quickly, but may proceed without the compound.

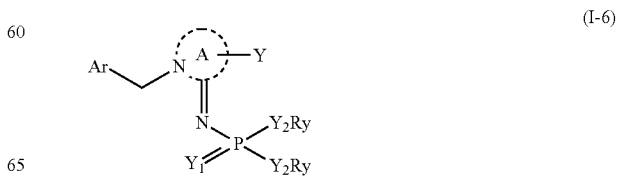

(I-6)

The compound represented by Formula (I-6) [the definition of Ar, A, Y, Y₁, Y₂, and R_y has the same meaning as the definition described above] may be obtained by reacting according to Phosphorus, sulfur, and silicon and the related elements (2006) 181, 2337-2344.

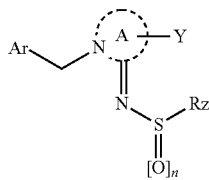

(I-7)

The compound represented by Formula (I-7) [the definition of Ar, A, Y, R_y and n has the same meaning as the definition described above] may be obtained by reacting a compound represented by the following Formula (II-7a) with a compound represented by ArCH₂X [the definition of Ar has the same meaning as the definition described above, and X represents a halogen atom or OTs, OMs and the like] in the presence or absence of a base.

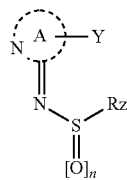

(II-7a)

When the reaction is performed in the presence of a base, it is possible to use, for example, an alkali metal hydride such as sodium hydride and the like; a carbonate such as potassium carbonate or sodium carbonate and the like; an alkali metal hydroxide such as potassium hydroxide, sodium hydroxide and the like; tertiary amines such as triethylamine, 1,8-diazabicyclo[4.3.0]non-5-ene and the like; and unsubstituted or substituent-containing pyridines, such as pyridine, 4-dimethylaminopyridine and the like; as the base.

The reaction may be performed without a solvent or using a solvent which does not affect the reaction, and when the solvent is used, it is possible to use solvents such as, for example, amides such as N,N-dimethylformamide and N,N-dimethylacetamide; nitriles such as acetonitrile; sulfoxides such as dimethyl sulfoxide; ethers such as diethyl ether and tetrahydrofuran; esters such as ethyl acetate and butyl acetate; aromatic hydrocarbons such as benzene, xylene and toluene; alcohols such as methanol, ethanol, propanol and isopropyl alcohol; ketones such as acetone and methyl ethyl ketone; aliphatic hydrocarbons such as hexane, heptane and octane; and halogen hydrocarbons such as dichloromethane, chloroform, chlorobenzene and dichlorobenzene; either alone or in combination of two or more thereof, but N,N-dimethylformamide and the like are preferably used. The reaction may be performed usually at from 0° C. to 200° C., and it is preferred that reagents are added at from 20° C. to 40° C. and the reaction is performed at from 60° C. to 80° C.

The compound represented by Formula (II-7a) may be obtained by reacting a compound represented by (II-7b) [X represents a halogen atom, and the definition of R_z and n has the same meaning as the definition described above] with a compound represented by in the following Formula (III) in the presence or absence of a base.

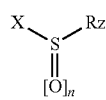

(II-7b)

When the reaction is performed in the presence of a base, it is possible to use, for example, an alkali metal hydride such as sodium hydride and the like; a carbonate such as potassium carbonate or sodium carbonate and the like; an alkali metal hydroxide such as potassium hydroxide, sodium hydroxide and the like; tertiary amines such as triethylamine, 1,8-diazabicyclo[4.3.0]non-5-ene and the like; and unsubstituted or substituent-containing pyridines, such as pyridine, 4-dimethylaminopyridine and the like; as the base.

The reaction may be performed without a solvent or using a solvent which does not affect the reaction, and when the solvent is used, it is possible to use solvents such as, for example, amides such as N,N-dimethylformamide and N,N-dimethylacetamide, nitriles such as acetonitrile; sulfoxides such as dimethyl sulfoxide; ethers such as diethyl ether and tetrahydrofuran; esters such as ethyl acetate and butyl acetate; aromatic hydrocarbons such as benzene, xylene and toluene; alcohols such as methanol, ethanol, propanol and isopropyl alcohol; ketones such as acetone and methyl ethyl ketone; aliphatic hydrocarbons such as hexane, heptane and octane; and halogen hydrocarbons such as dichloromethane, chloroform, chlorobenzene and dichlorobenzene; either alone or in combination of two or more thereof, but N,N-dimethylformamide and the like are preferably used.

The reaction may be performed usually at from 0° C. to 200° C., and it is preferred that reagents are added at from 20° C. to 40° C. and the reaction is performed at from 60° C. to 80° C.

The compound represented by Formula (I-7) may be obtained by reacting a compound represented by (II-7b) with a compound represented by in the above Formula (IV) in the presence or absence of a base.

When the reaction is performed in the presence of a base, it is possible to use, for example, an alkali metal hydride such as sodium hydride and the like; a carbonate such as potassium carbonate or sodium carbonate and the like; an alkali metal hydroxide such as potassium hydroxide, sodium hydroxide and the like; tertiary amines such as triethylamine, 1,8-diazabicyclo[4.3.0]non-5-ene and the like; and unsubstituted or substituent-containing pyridines, such as pyridine, 4-dimethylaminopyridine and the like; as the base.

The reaction may be performed without a solvent or using a solvent which does not affect the reaction, and when the solvent is used, it is possible to use solvents such as, for example, amides such as N,N-dimethylformamide and N,N-dimethylacetamide; nitriles such as acetonitrile; sulfoxides such as dimethyl sulfoxide; ethers such as diethyl ether and tetrahydrofuran; esters such as ethyl acetate and butyl acetate; aromatic hydrocarbons such as benzene, xylene and toluene; alcohols such as methanol, ethanol, propanol and isopropyl alcohol; ketones such as acetone and methyl ethyl ketone; aliphatic hydrocarbons such as hexane, heptane and octane; and halogen hydrocarbons such as dichloromethane, chloroform, chlorobenzene and dichlorobenzene; either alone or in combination of two or more thereof, but N,N-dimethylformamide and the like are preferably used.

The reaction may be performed usually at from 0° C. to 200° C., and it is preferred that the reaction is performed at from 0° C. to 80° C.

Examples of a substituent that may be substituted of "a phenyl group which may be substituted" and "a 5- to 6-membered heterocycle which may be substituted", which are represented by Ar, include a halogen atom, a C1 to C4 alkyl group which may be substituted with a halogen atom, a C1 to C4 alkyloxy group which may be substituted with a halogen atom, a hydroxyl group, a cyano group, a nitro group and the like, preferably a halogen atom, a trifluoromethyl group and a cyano group, and particularly preferably a halogen atom.

Specific examples of the "a phenyl group which may be substituted" represented by Ar of a nitrogen-containing heterocyclic derivative compound having a 2-imino group represented by Formula (I) include a phenyl group and a 3-cyano phenyl group.

"A 5- to 6-membered heterocycle which may be substituted", represented by Ar of a nitrogen-containing heterocyclic derivative compound having a 2-imino group represented by Formula (I) represents an aromatic 5- to 6-membered heterocycle including one or two of a heteroatom such as an oxygen atom, a sulfur atom or a nitrogen atom, specific examples thereof include a pyridine ring, a pyrazine ring, a pyrimidine ring, a pyridazine ring, a thiazole ring, an oxazole ring and the like, and preferable aspects thereof include a 6-chloro-3-pyridyl group, a 6-chloro-5-fluoro-3-pyridyl group, a 6-bromo-3-pyridyl group, a 6-fluoro-3-pyridyl group, a 6-trifluoromethyl-3-pyridyl group, a 6-chloro-3-pyridazinyl group, a 5-chloro-2-pyrazinyl group, a 2-chloro-5-pyrimidinyl group, a 2-chloro-5-thiazolyl group, a 2-chloro-4-pyridyl group, and more preferably a 6-chloro-3-pyridyl group, a 6-fluoro-3-pyridyl group, a 6-chloro-5-fluoro-3-pyridyl group, a 6-bromo-3-pyridyl group and a 2-chloro-5-pyrimidinyl group.

Specific examples of "a 4- to 10-membered heterocycloalkyl group" represented by Ar of a nitrogen-containing hetero ring derivative having a 2-imino group represented by Formula (I) include a 2-tetrahydrofuranyl group, a 3-tetrahydrofuranyl group and the like and preferably a 3-tetrahydrofuranyl group.

"A 5- to 10-membered heterocycle having a unsaturated bond including one or more nitrogen atoms", which A of a nitrogen-containing heterocyclic derivative having a 2-imino group represented by Formula (I) represents, means that

in Formula (I) represents any one ring represented by each of the following Formulae A-1 to A-40. In each formula, the end of a double bond is the substitution position of a nitrogen atom.

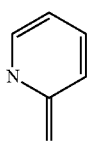
A-1

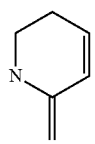
A-2

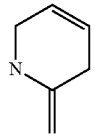
A-3

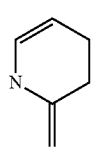
A-4

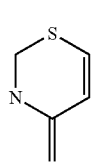
A-5

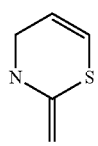
A-6

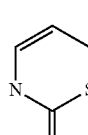
A-7

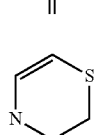
A-8

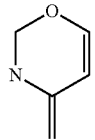
A-9

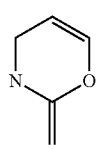
A-10

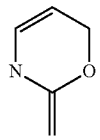
A-11

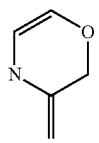 A-12
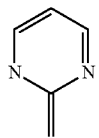 A-13
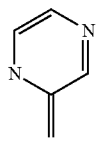 A-14
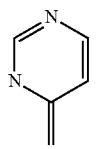 A-15
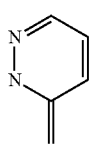 A-16
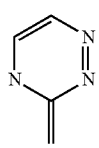 A-17
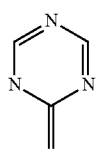 A-18
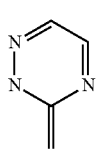 A-19
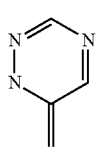 A-20
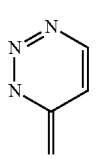 A-21
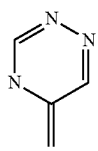 A-22
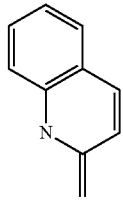 A-23
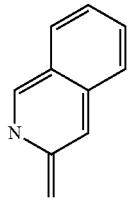 A-24
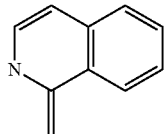 A-25
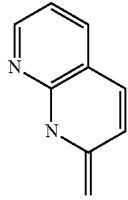 A-26
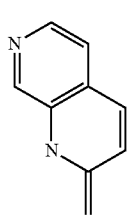 A-27
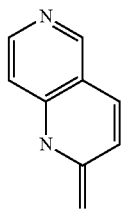 A-28
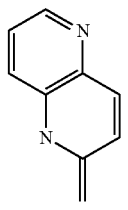 A-29

A-30 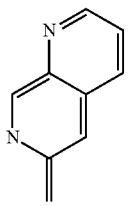

A-31 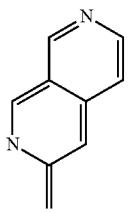

A-32 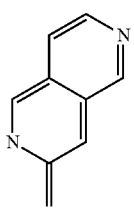

A-33 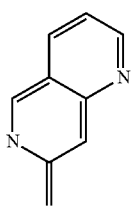

A-34 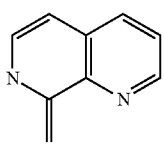

A-35 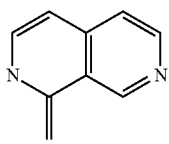

A-36 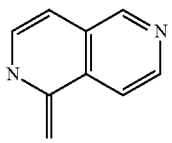

A-37 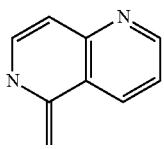

A-38 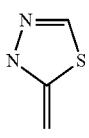

A-39 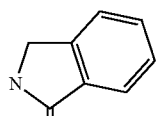

A-40 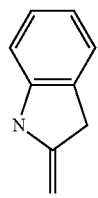

The ring is preferably the ring of Formulae A-1, A-13, A-14, A-15, A-16, A-23, A-25, A-38 and A-39 and more preferably the ring of Formula A-1.

"A C1 to C6 alkyl group which may be substituted with a halogen atom", which Y represents, is an alkyl group having 1 to 6 carbon atoms, which is chained, branched, cyclic or combination thereof, and the upper limit of the number of halogen atoms which may be substituted is the number of hydrogen atoms which the alkyl group has. When a branched or cyclic alkyl group is included, it is obvious that the number of carbons is 3 or more.

Specific examples of "a C1 to C6 alkyloxy group which may be substituted with a halogen atom" which Y represents include a methoxy group, an ethoxy group, a trifluoromethyloxy group and a difluoromethyloxy group.

A preferred aspect of Y is a hydrogen atom, a halogen atom or a cyano group, preferably a hydrogen atom or a halogen atom and more preferably a hydrogen atom.

A preferred aspect of R is a group represented by the Formula (a), (c) and (d) described above.

in Formula (I), "a substituted C1 to C6 alkyl group" which $R_1$ represents is an alkyl group having 1 to 6 carbon atoms, which is chained, branched, cyclic or combination thereof, and the upper limit of the number of substituted substituents is the number of hydrogen atoms which the alkyl group has. Examples of the substituted substituent include a halogen atom, a hydroxyl group, a cyano group, a nitro group, a phenyl group (this phenyl group may be substituted with a C1 to C4 alkyl group which may be substituted with a halogen, a C1 to C4 alkyloxy group which may be substituted with a halogen, a hydroxyl group, or a halogen atom), a phenoxy group (this phenyl group may be substituted with a C1 to C4 alkyl group which may be substituted with a halogen, a C1 to C4 alkyloxy group which may be substituted with a halogen, a hydroxyl group, or a halogen atom), a benzyloxy group (the phenyl group in this benzyloxy group may be substituted with a C1 to C4 alkyl group which may be substituted with a halogen, a C1 to C4 alkyloxy group which may be substituted with a halogen, a hydroxyl group, or a halogen atom), and the like. Specific examples thereof include a 1,1,1-trifluoroethyl group, a trifluoromethyl group, a trichloromethyl group, a difluorochloromethyl group, a difluoromethyl group, a dichloromethyl group, a dibromomethyl group, a chloromethyl group, a difluoroethyl group, a dichloroethyl group, a 2,2,2-trifluoroethyl group, a pentafluoroethyl group, a difluorocyclopropyl group, a 2-cyanoethyl group, a 2-nitroethyl group and the like. A 1,1,1-trifluoroethyl group, a trifluoromethyl group, a difluoromethyl group, a difluoromethyl group and a pentafluoroethyl group are preferred, a trifluoromethyl group, a difluorochloromethyl group, a difluoromethyl group and a pentafluoroethyl group are more preferred, and a trifluoromethyl group are particularly preferred.

In Formula (I), "a C1 to C6 alkyl group which may be substituted with a halogen atom" which $R_3$, $R_5$, $R_7$, $R_y$, and $R_z$ represent is an alkyl group having 1 to 6 carbon atoms, which is chained, branched, cyclic or combination thereof, and the upper limit of the number of substituted halogen atoms is the number of hydrogen atoms which the alkyl group has. When a branched or cyclic alkyl group is included, it is obvious that the number of carbons is 3 or more. Specific examples thereof include a methyl group, an ethyl group, an n-propyl group, an isopropyl group, an n-butyl group, a t-butyl group, a cyclopropyl group, a cyclopentyl group, a cyclohexyl group, a trifluoromethyl group, a trichloromethyl group, a difluorochloromethyl group, a difluoromethyl group, a dichloromethyl group, a dibromomethyl group, a chloromethyl group, a difluoroethyl group, a dichloroethyl group, a 2,2,2-trifluoroethyl group, a pentafluoroethyl group, a difluorocyclopropyl group, a trifluoroisopropyl group, and a hexafluoroisopropyl group, and the like.

$R_3$ is each preferably an ethyl group, an isopropyl group, a cyclopropyl group, a trifluoromethyl group, a difluorochloromethyl group, a difluoromethyl group and a pentafluoroethyl group, more preferably a trifluoromethyl group, a difluorochloromethyl group, a difluoromethyl group and a pentafluoroethyl group, and particularly preferably a trifluoromethyl group. $R_5$ is preferably a trifluoromethyl group, a trichloromethyl group, a dichloromethyl group, a difluoromethyl group, a difluorochloromethyl group, a chloromethyl group and a pentafluoroethyl group, more preferably a trifluoromethyl group, a difluoromethyl group, a difluorochloromethyl group and a pentafluoroethyl group, and particularly preferably a trifluoromethyl group. $R_7$ is preferably a trifluoromethyl group, a trichloromethyl group, a dichloromethyl group, a difluoromethyl group, a difluorochloromethyl group, a chloromethyl group and a pentafluoroethyl group, more preferably a trifluoromethyl group, a difluoromethyl group, a difluorochloromethyl group and a pentafluoroethyl group, and particularly preferably a trifluoromethyl group. $R_y$ is preferably a methyl group, ethyl group, propyl group or isopropyl group. $R_z$ is preferably a methyl group or trifluoromethyl group.

"A C1 to C6 alkyl group which may be substituted with a halogen atom", which $R_2$ represents, is an alkyl group having 1 to 6 carbon atoms, which is chained, branched, cyclic or combination thereof, and the upper limit of the number of substituted halogen atoms is the number of hydrogen atoms which the alkyl group has. When a branched or cyclic alkyl group is included, it is obvious that the number of carbons is 3 or more. Specific examples thereof include a trifluoromethyl group, a trichloromethyl group, a difluorochloromethyl group, a difluoromethyl group, a dichloromethyl group, a dibromomethyl group, a chloromethyl group, a difluoroethyl group, a dichloroethyl group, a 2,2,2-trifluoroethyl group, a pentafluoroethyl group, a difluorocyclopropyl group, a 1-(trifluoromethyl)ethyl group, a 1-trifluoromethyl-2,2,2-trifluoroethyl group, a pentafluoroethyl group, and a difluorocyclopropyl group, and the like, and preferred examples thereof include a 2,2,2-trifluoroethyl group, a 1-(trifluoromethyl) ethyl group and a 1-trifluoromethyl-2,2,2-trifluoroethyl group.

"A C1 to C6 alkyl group which may be substituted" which $R_4$ and $R_6$ represent is an alkyl group having 1 to 18 carbon atoms, which is chained, branched, cyclic or combination thereof, and the upper limit of the number of substituents which may be substituted is the number of hydrogen atoms which the alkyl group has. When a branched or cyclic alkyl group is included, it is obvious that the number of carbons is 3 or more.

Examples of the substituent which may be substituted include a halogen atom, a hydroxyl group, a cyano group, a nitro group and the like. Specific examples thereof include a methyl group, an ethyl group, an n-propyl group, an isopropyl group, an n-butyl group, an s-butyl group, a t-butyl group, a 3-methyl-2-butyl group, a 3-pentyl group, a 4-heptyl group, a cyclopropyl group, a cyclobutyl group, a cyclopentyl group, a cyclohexyl group, an n-octyl group, an n-tridecyl group, an n-hexadecyl group, an n-octadecyl group, a trifluoromethyl group, a trichloromethyl group, a difluorochloromethyl group, a difluoromethyl group, a dichloromethyl group, a dibromomethyl group, a chloromethyl group, a difluoroethyl group, a dichloroethyl group, a 2,2,2-trifluoroethyl group, a pentafluoroethyl group, a difluorocyclopropyl group, a 2-hydroxyethyl group, a 2-hydroxy-n-propyl group, a 3-hydroxy-n-propyl group, a 2,3-dihydroxy-n-propyl group, a cyanomethyl group, a 2-cyanoethyl group, a 2-nitroethyl group and the like.

$R_4$ is each preferably a methyl group, an ethyl group, a 2,2,2-trifluoroethyl group, a 2,2-difluoroethyl group, an n-propyl group, an isopropyl group, a cyclopropyl group, a t-butyl group, a cyclopentyl group, a cyclohexyl group and a 2-hydroxyethyl group, and more preferably a methyl group, an ethyl group and a cyclopropyl group. $R_6$ is preferably a methyl group, an ethyl group, an isopropyl group a cyclopropyl group, a t-butyl group and a cyanomethyl group, and more preferably a methyl group, an ethyl group, a cyclopropyl group and a t-butyl group.

"A C1 to C6 alkyl group which may be substituted with a halogen atom", which $R_{4a}$, $R_{4b}$, $R_{4c}$, $R_{4d}$, $R_{4e}$, $R_{4f}$, $R_{6a}$, $R_{6b}$, $R_{6c}$, $R_{6d}$, $R_{6e}$, $R_{6f}$, $R_{6g}$, $R_{6h}$, $R_{6i}$, $R_{6j}$ and $R_{6k}$ represent, is an alkyl group having 1 to 6 carbon atoms, which is chained, branched, cyclic or combination thereof, and the upper limit of the number of substituted halogen atoms is the number of hydrogen atoms which the alkyl group has. When a branched or cyclic alkyl group is included, it is obvious that the number of carbons is 3 or more. Specific examples thereof include a methyl group, an ethyl group, an n-propyl group, an isopropyl group, an n-butyl group, a t-butyl group, a cyclopropyl group, a cyclopentyl group, a cyclohexyl group, a trifluoromethyl group, a trichloromethyl group, a difluorochloromethyl group, a difluoromethyl group, a dichloromethyl group, a dibromomethyl group, a chloromethyl group, a difluoroethyl group, a 2-chloroethyl group, a dichloroethyl group, a 2,2,2-trifluoroethyl group, a pentafluoroethyl group, a difluorocyclopropyl group and the like. $R_{6a}$ is preferably a methyl group, an ethyl group, an isopropyl group and a cyclopropyl group. $R_{6b}$ is preferably a methyl group.

"A C2 to C6 alkenyl group which may be substituted with a halogen atom", which $R_1$, $R_2$, $R_3$, $R_4$, $R_{4a}$, $R_{4b}$, $R_{4c}$, $R_{4d}$, $R_{4e}$, $R_{4f}$, $R_5$, $R_6$, $R_{6a}$, $R_{6b}$, $R_{6c}$, $R_{6d}$, $R_{6e}$, $R_{6f}$, $R_{6g}$, $R_{6h}$, $R_{6i}$, $R_{6j}$, $R_{6k}$, $R_7$, $R_y$ and $R_z$ represent, is an alkenyl group having 2 to 6 carbon atoms, which is chained, branched, cyclic or combination thereof, and the upper limit of the number of substituted halogen atoms is the number of hydrogen atoms which the alkenyl group has. When a branched or cyclic alkenyl group is included, it is obvious that the number of carbons is 3 or more. Specific examples thereof include an ethenyl group, a 1-propenyl group, a 2-propenyl group, a 2-fluoro-1-propenyl group, a 2-methyl-1-propenyl group and the like, and preferred examples thereof include an ethenyl group.

"A C2 to C6 alkynyl group which may be substituted with a halogen atom", which $R_1$, $R_2$, $R_3$, $R_4$, $R_{4a}$, $R_{4b}$, $R_{4c}$, $R_{4d}$, $R_{4e}$, $R_{4f}$, $R_5$, $R_6$, $R_{6a}$, $R_{6b}$, $R_{6c}$, $R_{6d}$, $R_{6e}$, $R_{6f}$, $R_{6g}$, $R_{6h}$, $R_{6i}$, $R_{6j}$, $R_{6k}$, $R_7$, $R_y$ and $R_z$ represent, is an alkynyl group having 2 to 6 carbon atoms, which is chained, branched, cyclic or combination thereof, and the upper limit of the number of substituted halogen atoms is the number of hydrogen atoms which the alkynyl group has. When a branched or cyclic alkynyl group is included, it is obvious that the number of carbons is 3 or more. Specific examples thereof include a 1-propynyl group, a 2-propynyl group, a 1-butynyl group, a 2-butynyl group, a 1-pentynyl group, a 2-pentynyl group, a 3-pentynyl group and the like, and preferred examples thereof include a 1-propynyl group, a 2-propynyl group and a 2-butynyl group.

The (C6 to C10) aryl of "a substituted or unsubstituted (C6 to C10) aryl group, a substituted or unsubstituted (C6 to C10) aryl (C1 to C6) alkyl group, a substituted or unsubstituted (C6 to C10) aryl (C2 to C6) alkenyl group and a substituted or unsubstituted (C6 to C10) aryl (C2 to C6) alkynyl group", which $R_3$, $R_4$, $R_{4a}$, $R_{4b}$, $R_{4c}$, $R_5$, $R_6$, $R_{6a}$, $R_{6b}$, $R_{6c}$, $R_7$, $R_y$ and $R_z$ represent, specifically represents a phenyl group and a naphthyl group, and the (C1 to C6) alkyl group, the (C2 to C6) alkenyl group and the (C2 to C6) alkynyl group may have a straight chain, branch or ring. Examples of the substituent which may be substituted with an aryl group include a halogen atom, a C1 to C4 alkyl group which may be substituted with halogen, a C1 to C4 alkyloxy group which may be substituted with halogen, a C3 to C6 cyclic alkyl group, a methylsulfonyl group, a methoxy group, a nitro group, a cyano group and the like. Specific examples thereof include a phenyl group, a benzyl group, a 2-phenylethyl group, a 2-phenylethenyl group, a 2-phenylethynyl group, a 4-methylphenyl group, a 2-cyanophenyl group, a 3-chlorophenyl group, a 4-methoxyphenyl group, a 3-cyanophenyl group, 1,1-diphenylmethyl group, a naphthylethyl group, a naphthylpropyl group and the like, and preferred examples thereof include a benzyl group and a 2-phenylethyl group, a naphthylethyl group, a naphthylpropyl group.

The (C1 to C6) alkyl group, (C2 to C6) alkenyl group and (C2 to C6) alkenyl group of "a substituted or unsubstituted phenoxy (C1 to C6) alkyl group, a substituted or unsubstituted phenoxy (C2 to C6) alkenyl group and a substituted or unsubstituted phenoxy (C2 to C6) alkynyl group", which $R_3$, $R_4$, $R_{4a}$, $R_{4b}$, $R_{4c}$, $R_5$, $R_6$, $R_{6a}$, $R_{6b}$, $R_{6c}$, $R_7$, $R_y$ and $R_z$ represent, may have a straight chain, branch or ring. Examples of the substituent which may be substituted with a phenoxy group include a halogen atom, a C1 to C4 alkyl group which may be substituted with halogen, a C1 to C4 alkyloxy group which may be substituted with halogen, a C3 to C6 cyclic alkyl group, a methylsulfonyl group, a methoxy group, a nitro group, a cyano group and the like. Specific examples thereof include a phenoxy group, a phenoxymethyl group, a 2-phenoxyethyl group, a 2-phenoxyethenyl group, a 2-phenoxyethynyl group, a 4-chlorophenoxy group, a 2-methylphenoxy group and the like, and preferred examples thereof include a 2-phenoxyethyl group.

The 5- to 10-membered heterocycle of "a substituted or unsubstituted 5- to 10-membered heterocycle, a substituted or unsubstituted 5- to 10-membered heterocycle (C1 to C6) alkyl group, a substituted or unsubstituted 5- to 10-membered heterocycle (C2 to C6) alkenyl group and a substituted or unsubstituted 5- to 10-membered heterocycle (C2 to C6) alkynyl group", which $R_3$, $R_4$, $R_{4a}$, $R_{4b}$, $R_{4c}$, $R_5$, $R_6$, $R_{6a}$, $R_{6b}$, $R_{6c}$, $R_7$, $R_y$ and $R_z$ represent, represents a ring including a hetero atom, such as an oxygen atom, a sulfur atom or a nitrogen atom as an atom constituting 1 to 4 rings, and examples thereof include a furanyl group, a thienyl group, a pyridyl group, a pyrrolidinyl group, a piperidinyl group, a piperazinyl group, a pyrimidinyl group, a morpholinyl group, a thiazolyl group, an imidazolyl group, a triazolyl group, a tetrahydrofuranyl group, a quinolinyl group and the like. Examples of the substituent which may be substituted with a heterocycle include a halogen atom, a C1 to C4 alkyl group which may be substituted with halogen, a C1 to C4 alkyloxy group which may be substituted with halogen, a C3 to C6 cyclic alkyl group, a methylsulfonyl group, a methoxy group, a nitro group, a cyano group and the like. The (C1 to C6) alkyl group, (C2 to C6) alkenyl group and (C2 to C6) alkenyl group may have a straight chain, branch or ring. Specific examples thereof include a 2-pyridyl group, a 3-pyridyl group, a 4-pyridyl group, a 2-pyridylmethyl group, a 3-pyridylmethyl group, a 4-pyridylmethyl group, a 2-(4-pyridyl)ethenyl group, a 2-(4-pyridyl)ethynyl group, a 2-furanylmethyl group, a 2-thienylmethyl group, a 2-tetrahydrofuranylmethyl group and the like, and preferred examples thereof include a 2-pyridylmethyl group, a 3-pyridylmethyl group, a 4-pyridylmethyl group, a 2-furanylmethyl group, a 2-thienylmethyl group and a 2-tetrahydrofuranylmethyl group.

The (C1 to C4) alkoxy of "a (C1 to C4) alkoxy (C1 to C5) alkyl group, a (C1 to C4) alkoxy (C2 to C5) alkenyl group and a (C1 to C4) alkoxy (C2 to C5) alkynyl group", which $R_3$, $R_4$, $R_{4a}$, $R_{4b}$, $R_{4c}$, $R_5$, $R_6$, $R_{6a}$, $R_{6b}$, $R_{6c}$, $R_{6e}$, $R_{6f}$, $R_7$ and $R_z$ represent, represents a (C1 to C4) alkyloxy, alkenyloxy and alkynyloxy having a straight chain, branch or ring. Specific examples thereof include a methoxymethyl group, a 2-methoxyethyl group, an ethoxymethyl group, a 2-ethoxyethyl group, a 3-methoxy-2-propenyl group, a 3-methoxy-2-propynyl group and the like. $R_4$ is preferably a 2-methoxyethyl group.

The (C1 to C4) alkylthio of "a (C1 to C4) alkylthio (C1 to C5) alkyl group, a (C1 to C4) alkylthio (C2 to C5) alkenyl group and a (C1 to C4) alkylthio (C2 to C5) alkynyl group", which $R_3$, $R_4$, $R_{4a}$, $R_{4b}$, $R_{4c}$, $R_5$, $R_6$, $R_{6a}$, $R_{6b}$, $R_{6c}$, $R_{6e}$, $R_{6f}$, $R_7$ and $R_z$ represent, represents a (C1 to C4) alkylthio, alkenylthio and alkynylthio having a straight chain, branch or ring. Examples thereof include a methylthiomethyl group, a 2-methylthioethyl group, an ethylthiomethyl group, a 2-ethylthioethyl group, a 3-methylthio-2-propenyl group, a 3-methylthio-2-propynyl group and the like. $R_4$ is preferably a 2-methylthioethyl group.

The (C6 to C10) aryl of "a substituted or unsubstituted (C6 to C10) aryl group", which $R_2$, $R_{4d}$, $R_{4e}$, $R_{4f}$, $R_{6d}$, $R_{6e}$, $R_{6f}$, $R_{6g}$, $R_{6h}$, $R_{6i}$, $R_{6j}$ and $R_{6k}$ represent, specifically represents a phenyl group and a naphthyl group, and the (C1 to C6) alkyl group, (C2 to C6) alkenyl group and (C2 to C6) alkenyl group may have a straight chain, branch or ring. Examples of the substituent which may be substituted with an aryl group include a halogen atom, a C1 to C4 alkyl group which may be substituted with halogen, a C1 to C4 alkyloxy group which may be substituted with halogen, a C3 to C6 cyclic alkyl group, a methylsulfonyl group, a methoxy group, a nitro group, a cyano group and the like. Specific examples thereof include a phenyl group, a 2-methylphenyl group, a 3-methoxyphenyl group, a 4-nitrophenyl group, a 4-cyanophenyl group and the like.

The 5- to 10-membered heterocycle of "a substituted or unsubstituted 5- to 10-membered heterocycle", which $R_2$, $R_{4d}$, $R_{4e}$, $R_{4f}$, $R_{6d}$, $R_{6e}$, $R_{6f}$, $R_{6g}$ and $R_{6h}$ represent, represents a ring including a hetero atom, such as an oxygen atom, a sulfur atom or a nitrogen atom as an atom constituting 1 to 4 rings, and examples thereof include a furanyl group, a thienyl group, a pyridyl group, a pyrrolidinyl group, a piperidinyl group, a piperazinyl group, a pyrimidinyl group, a morpholinyl group, a thiazolyl group, an imidazolyl group, a triazolyl group, a tetrahydrofuranyl group, a quinolinyl group and the like. Examples of the substituent which may be substituted with a heterocycle include a halogen atom, a C1 to C4 alkyl group which may be substituted with halogen, a C1 to C4 alkyloxy group which may be substituted with halogen, a C3 to C6 cyclic alkyl group, a methylsulfonyl group, a methoxy group, a nitro group, a cyano group and the like. Specific examples thereof include a 2-pyridyl group, a 3-pyridyl group, a 4-pyridyl group, a 2-furanyl group, a 2-thienyl group, a 2-tetrahydrofuranyl group and the like.

As a preferred aspect of a compound represented by Formula (I),

R represents the following Formula (a),

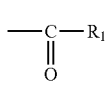

(a)

Ar represents a 6-chloro-3-pyridyl group, a 2-chloro-5-thiazolyl group, a 6-chloro-5-fluoro-3-pyridyl group, a 6-fluoro-3-pyridyl group, a 6-bromo-3-pyridyl group, a 2-chloro-5-pyrimidinyl group, a 6-trifluoromethyl-3-pyridyl group and a 2-chloro-5-pyrimidinyl group, A represents a ring represented by A-1, A-13, A-14, A-15, A-16, A-23 and A-38, Y represents a hydrogen atom and a 3-cyano group, and $R_1$ represents a trifluoromethyl group, a difluoromethyl group, a chlorodifluoromethyl group, a pentafluoroethyl group, a trifluoroethyl group, an ethenyl group and a 2-propynyl group.

As another preferred aspect of a compound represented by Formula (I),

R represents the following Formula (c),

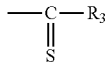

(c)

Ar represents a 6-chloro-3-pyridyl group, a 2-chloro-5-thiazolyl group, a 6-chloro-5-fluoro-3-pyridyl group, a 6-fluoro-3-pyridyl group, a 6-bromo-3-pyridyl group, a 2-chloro-5-pyrimidyl group and a 6-trifluoromethyl-3-pyridyl group, A represents a ring represented by A-1, Y represents a hydrogen atom, and $R_3$ represents a trifluoromethyl group, a difluoromethyl group, a chlorodifluoromethyl group and a pentafluoroethyl group.

As still another preferred aspect of a compound represented by Formula (I),

R represents the following Formula (d),

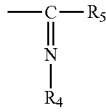

(d)

Ar represents a 6-chloro-3-pyridyl group, a 6-chloro-5-fluoro-3-pyridyl group, a 6-fluoro-3-pyridyl group, a 6-bromo-3-pyridyl group and a 2-chloro-5-pyrimidyl group, A represents a ring represented by A-1, Y represents a hydrogen atom, $R_4$ represents a hydrogen atom, a methyl group, an ethyl group, an n-propyl group, an isopropyl group, a cyclopropyl group, a cyclobutyl group, a cyclohexyl group, and cyclopentyl group, and $R_5$ represents a trifluoromethyl group, a difluoromethyl group, a chlorodifluoromethyl group and a pentafluoroethyl group.

As yet another preferred aspect of a compound represented by Formula (I),

R represents the following Formula (e) group

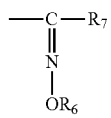

(e)

Ar represents a 6-chloro-3-pyridyl group, a 6-chloro-5-fluoro-3-pyridyl group, a 6-fluoro-3-pyridyl group, a 6-bromo-3-pyridyl group and a 2-chloro-5-pyrimidyl group, A represents a ring represented by A-1, Y represents a hydrogen atom, and $R_6$ represents a hydrogen atom, a methyl group, an ethyl group, a 2-propenyl group, a methylcarbonyl group, an ethylcarbonyl group, a cyclopropylcarbonyl group, an ethenylcarbonyl group, a 2-propynylcarbonyl group, a benzoyl group, a 3-pyridylcarbonyl group, a methyloxycarbonyl group and a phenyloxycarbonyl group, and $R_7$ represents a trifluoromethyl group, a difluoromethyl group, a chlorodifluoromethyl group and a pentafluoroethyl group.

Specific examples of the compound of Formula (I) include a compound represented by a combination of the following Table A and Table B.

TABLE 1

| compound No. | Ar | A | Y | R |
|---|---|---|---|---|
| 250-2 | 6-Chloro-3-pyridyl | A-38 | H | COCF3 |
| 444-2 | 2-Chloro-5-thiazolyl | A-39 | H | COCF3 |
| 190-2 | 6-Chloro-3-pyridyl | A-13 | H | COCF3 |
| 201-2 | 6-Chloro-3-pyridyl | A-14 | H | COCF3 |
| 223-2 | 6-Chloro-3-pyridyl | A-16 | H | COCF3 |
| 146-2 | 6-Chloro-3-pyridyl | A-1 | 3-OH | COCF3 |
| 224-2 | 2-Chloro-5-thiazolyl | A-15 | H | COCF3 |
| 102-2 | 6-Chloro-3-pyridyl | A-1 | 3-CN | COCF3 |
| 212-2 | 6-Chloro-3-pyridyl | A-15 | H | COCF3 |
| 1-20 | 8-Chloro-3-pyridyl | A-15 | H | CSCF3 |
| 12-2 | 2-Chloro-4-pyridyl | A-1 | H | COCF3 |
| 213-2 | 2-chloro-5-thiazolyl | A-15 | H | COCF3 |
| 1-17 | 6-Chloro-3-pyridyl | A-1 | H | COOCH2CF3 |
| 1-18 | 6-Chloro-3-pyridyl | A-1 | H | COOCH(Me)CF3 |
| 1-19 | 6-Chloro-3-pyridyl | A-1 | H | COOCH(CF3)2 |
| 7-2 | 5-Chloropyrazin-2-yl | A-1 | H | COOF3 |
| 1-12 | 6-Chloro-3-pyridyl | A-1 | H | COOCH2CF3 |
| 168-2 | 6-Chloro-3-pyridyl | A-1 | 5-OH | COCF3 |
| 1-21 | 6-Chloro-3-pyridyl | A-1 | H | CSCHF2 |
| 3-20 | 6-Fluoro-3-pyridyl | A-1 | H | CSCF3 |
| 4-20 | 6-Bromo-3-pyridyl | A-1 | H | CSCF3 |
| 3-3 | 6-Fluoro-3-pyridyl | A-1 | H | COCHF2 |
| 4-3 | 6-Bromo-3-pyridyl | A-1 | H | COCHF2 |
| 5-5 | 6-Chloro-5-fluoro-3-pyridyl | A-1 | H | COCF2CF3 |
| 6-5 | 2-Chloro-5-pyrimidinyl | A-1 | H | COCF2CF3 |
| 1-22 | 6-Chloro-3-pyridyl | A-1 | H | CSCF2Cl |
| 1-23 | 6-Chloro-3-pyridyl | A-1 | H | CSCF2CF3 |

TABLE 1-continued

| compound No. | Ar | A | Y | R |
|---|---|---|---|---|
| 5-20 | 6-Chloro-3-fluoro-5-pyridyl | A-1 | H | CSCF3 |
| 5-3 | 6-Chloro-5-fluoro-3-pyridyl | A-1 | H | COCHF2 |
| 6-3 | 2-Chloro-5-pyrimidinyl | A-1 | H | COCHF2 |
| 6-2 | 6-Chloropyrazin-3-yl | A-1 | H | COCF3 |
| 6-4 | 6-Chloro-5-Fluoro-3-pyridyl | A-1 | H | COCF2Cl |
| 4-4 | 6-Bromo-3-pyridyl | A-1 | H | COCF2Cl |
| 6-4 | 2-Chloro-5-pyrimidinyl | A-1 | H | COCF2Cl |
| 4-5 | 6-Bromo-3-pyridyl | A-1 | H | COCF2CF3 |
| 2-20 | 2-Chloro-5-thiazolyl | A-1 | H | CSCF3 |
| 10-20 | 6-Trifluoromethyl-8-pyridyl | A-1 | H | CSCF3 |
| 3-4 | 6-Fluoro-3-pyridyl | A-1 | H | COCF2Cl |
| 3-5 | 6-Fluoro-3-pyridyl | A-1 | H | COCF2CF3 |
| 11-20 | 3-Tetrahydrofuranyl | A-1 | H | CSCF3 |
| 1-14 | 6-Chloro-3-pyridyl | A-1 | H | COCH•CH2 |
| 1-37 | 6-Chloro-3-pyridyl | A-1 | H | CSEt |
| 1-39 | 6-Chloro-3-pyridyl | A-1 | H | CS-i-Pr |
| 1-40 | 6-Chloro-3-pyridyl | A-1 | H | C5-cyclopropyl |
| 1-15 | 6-Chloro-3-pyridyl | A-1 | H | COCH2C≡CH |
| 1-35 | 6-Chloro-3-pyridyl | A-1 | H | C5CH2CH2Ph |
| 1-501 | 6-Chloro-3-pyridyl | A-1 | H | C(=NDEt)CF3 |
| 1-499 | 6-Chloro-3-pyridyl | A-1 | H | C(=NDH)CF3 |
| 1-510 | 6-Chloro-3-pyridyl | A-1 | H | C(=NDCH2Ph)CF3 |
| 1-511 | 6-Chloro-3-pyridyl | A-1 | H | C(=NDCOMe)CF3 |
| 1-519 | 6-Chloro-3-pyridyl | A-1 | H | C(=NDCO2Ph)CF3 |
| 1-523 | 6-Chloro-3-pyridyl | A-1 | H | C(=NDCOOMe)CF3 |

TABLE 2

| compound No. | Ar | A | Y | R |
|---|---|---|---|---|
| 1-528 | 6-Chloro-3-pyridyl | A-1 | H | C(=NOSO2Me)CF3 |
| 1-531 | 6-Chloro-3-pyridyl | A-1 | H | C(=NOSO2-(4-methylphenyl))CF3 |
| 1-507 | 6-Chloro-3-pyridyl | A-1 | H | C(=NOCH2CH=CH2)CF3 |
| 1-516 | 6-Chloro-3-pyridyl | A-1 | H | C(=NOCOCH=CH2)CF3 |
| 1-518 | 6-Chloro-3-pyridyl | A-1 | H | C(=NOCOCH2C≡CH)CF3 |

TABLE 2-continued

| compound No. | Ar | A | Y | R |
|---|---|---|---|---|
| 1-527 | 6-Chloro-3-pyridyl | A-1 | H | C(=NOCOOPh)FC3 |
| 1-521 | 6-Chloro-3-pyridyl | A-1 | H | C(=NOCO-3-pyr)CF3 |
| 1-43 | 6-Chloro-3-pyridyl | A-1 | H | C(=NEt)CF3 |
| 1-536 | 6-Chloro-3-pyridyl | A-1 | H | C(=NOCONHCH2Ph)CF3 |
| 1-42 | 6-Chloro-3-pyridyl | A-1 | H | C(=NMe)CF3 |
| 1-500 | 6-Chloro-3-pyridyl | A-1 | H | C(=NOMe)CF3 |
| 1-504 | 6-Chloro-3-pyridyl | A-1 | H | C(=NOtBu)CF3 |
| 1-534 | 6-Chloro-3-pyridyl | A-1 | H | C(=NOCONHnPr)CF3 |
| 1-535 | 6-Chloro-3-pyridyl | A-1 | H | C(=NOCONHCH2CH2Cl)CF3 |
| 1-72 | 6-Chloro-3-pyridyl | A-1 | H | C(=NCH2Ph)CF3 |
| 1-150 | 6-Chloro-3-pyridyl | A-1 | H | C(=NCH2CH2SMe)CF3 |
| 1-67 | 6-Chloro-3-pyridyl | A-1 | H | C(=NCH2CH2OH)CF3 |
| 1-515 | 6-Chloro-3-pyridyl | A-1 | H | C(=NOCO-cyclopropyl)CF3 |
| 1-56 | 6-Chloro-3-pyridyl | A-1 | H | C(=NCH2C≡CH)CF3 |
| 1-512 | 6-Chloro-3-pyridyl | A-1 | H | C(=NOCOCH2CH3)CF3 |
| 1-514 | 6-Chloro-3-pyridyl | A-1 | H | C(=NOCO-Iso-Pr)CF3 |
| 1-50 | 6-Chloro-3-pyridyl | A-1 | H | C(=N-cyclopropyl)CF3 |
| 1-114 | 6-Chloro-3-pyridyl | A-1 | H | C(=NCH2CH2OPh)CF3 |
| 1-46 | 6-Chloro-3-pyridyl | A-1 | H | C(=N-n-Pr)CF3 |
| 1-116 | 6-Chloro-3-pyridyl | A-1 | H | C(=NCH2-(2-pyridyl)CF3 |
| 1-119 | 6-Chloro-3-pyridyl | A-1 | H | C(=NCH2-(3-pyridyl)CF3 |
| 1-47 | 6-Chloro-3-pyridyl | A-1 | H | C(=N-n-Bu)CF3 |
| 1-55 | 6-Chloro-3-pyridyl | A-1 | H | C(=N—CH2CH=CH2)CF3 |
| 1-122 | 6-Chloro-3-pyridyl | A-1 | H | C(=NCH2-(2-thlenyl))CF3 |
| 1-45 | 6-Chloro-3-pyridyl | A-1 | H | C(=N-i-Pr)CF3 |
| 1-124 | 6-Chloro-3-pyridyl | A-1 | H | C(=NCH2-(2-furanyl))CF3 |
| 1-126 | 6-Chloro-3-pyridyl | A-1 | H | C(=NCH2-(2-tetrahydrofuranyl)CF3 |
| 1-64 | 6-Chloro-3-pyridyl | A-1 | H | C(=NCH2CN)CF3 |
| 1-146 | 6-Chloro-3-pyridyl | A-1 | H | C(=NCH2CH2OCH3)CF3 |
| 1-52 | 6-Chloro-3-pyridyl | A-1 | H | C(=N-cyclopentyl)CF3 |
| 1-121 | 6-Chloro-3-pyridyl | A-1 | H | C(=NCH2-(4-pyridyl)CF3 |
| 1-53 | 6-Chloro-3-pyridyl | A-1 | H | C(=N-cyclohexyl)CF3 |
| 1-76 | 6-Chloro-3-pyridyl | A-1 | H | C(=NCH2CH2Ph)CF3 |
| 267-2 | 6-Chloro-3-pyridyl | A-1 | H | COCF3 |
| 253-2 | 6-Chloro-3-pyridyl | A-1 | H | COCF3 |
| 251-2 | 6-Chloro-3-pyridyl | A-1 | H | COCF3 |
| 13-2 | 3-Cyanophenyl | A-1 | H | COCF3 |
| 1-1 | 6-Chloro-3-pyridyl | A-1 | H | CHO |
| 1-41 | 6-Chloro-3-pyridyl | A-1 | H | C(=NH)CF3 |

TABLE 3

| compound No. | Ar | A | Y | R |
|---|---|---|---|---|
| 1-647 | 6-Chloro-3-pyridyl | A-1 | H | COOCH2CH2CH=CH2 |
| 1-670 | 6-Chloro-3-pyridyl | A-1 | H | C(=NCH2CH2F)CF3 |
| 157-2 | 6-Chloro-3-pyridyl | A-1 | 4-OH | COCF8 |
| 1-10 | 6-Chloro-3-pyridyl | A-1 | H | CO(2,2-difluorocyclopropyl) |
| 580-2 | 6-chloro-3-pyridyl-N-oxide | A-1 | H | COCF3 |
| 1-671 | 6-Chloro-3-pyridyl | A-1 | H | C(=N(CH2)7CH3)CF3 |
| 1-658 | 6-Chloro-3-pyridyl | A-1 | H | C(=N(CH2)15CH3)CF3 |
| 1-659 | 6-Chloro-3-pyridyl | A-1 | H | C(=(CH2)11CH3)CF3 |
| 1-660 | 6-Chloro-3-pyridyl | A-1 | H | C(=NOH(CH3)CH2CH3)CF3 |
| 1-681 | 6-Chloro-3-pyridyl | A-1 | H | C(=NCH(CH2CH3)2)CF3 |
| 1-686 | 6-Chloro-3-pyridyl | A-1 | H | C(=NCH(CH2CH2CH3)2)CF3 |
| 1-681 | 6-Chloro-3-pyridyl | A-1 | H | C(=NCH(Ch3)CH2CH2CH3)CF3 |
| 1-662 | 6-Chloro-3-pyridyl | A-1 | H | C(=NCH(iso-propyl)CH3)CF3 |
| 1-663 | 6-Chloro-3-pyridyl | A-1 | H | C(=N(1-phenylethyl))CF3 |
| 1-664 | 6-Chloro-3-pyridyl | A-1 | H | C(=N-(1,2,3,4-tetrahydronaphthalen-1-yl))CF3 |
| 1-665 | 6-Chloro-3-pyridyl | A-1 | H | C(=N(1-(naphthalen-1-yl)ethyl))CF3 |
| 1-666 | 6-Chloro-3-pyridyl | A-1 | H | C(=N(1-(naphthalen-1-yl)propyl))CF3 |
| 1-667 | 6-Chloro-3-pyridyl | A-1 | H | C(=N(1-(furan-2-yl)ethyl))CF3 |
| 1-676 | 6-Chloro-3-pyridyl | A-1 | H | C(=NCH(C3H5)2)CF3 |
| 1-668 | 6-Chloro-3-pyridyl | A-1 | H | C(=N(3,3-dimethylbutan-2-yl))CF3 |
| 47-2 | 6-Chloro-3-pyridyl | A-1 | 6-F | COCF3 |
| 91-2 | 6-Chloro-3-pyridyl | A-1 | 6-Cl | COCF3 |
| 478-2 | 6-Chloro-3-pyridyl | A-1 | 6-CH3 | COCF3 |
| 470-2 | 2-Chloro-5-thiazolyl | A-1 | 6-CH3 | COCF3 |
| 1-51 | 6-Chloro-3-pyridyl | A-1 | H | C(=N-cyclobutyl)CF3 |

TABLE 3-continued

| compound No. | Ar | A | Y | R |
|---|---|---|---|---|
| 566-2 | 6-Chloro-3-pyridyl | A-1 | 6-CH3O | COCF3 |
| 468-2 | 3-tetrahydrofuranyl | A-1 | 6-CH3 | COCF3 |
| 511-2 | 6-Chloro-3-pyridyl | A-1 | 5-NO2 | COCF3 |
| 1-669 | 6-Chloro-3-pyridyl | A-1 | H | C(=N(1-thiophen-2-yl)ethyl))CF3 |
| 179-2 | 6-Chloro-3-pyridyl | A-1 | 6-OH | COCF3(互変異性体も示す) |
| 555-2 | 6-Chloro-3-pyridyl | A-1 | 5-CH3O | COCF3 |
| 577-2 | 2,6-dichrolo-3-pyridyl | A-1 | H | COCF3 |
| 544-2 | 6-Chloro-3-pyridyl | A-1 | 4-CH3O | COCF3 |
| 168-2 | 6-Chloro-3-pyridyl | A-1 | 5-OH | COCF3 |
| 1-644 | 6-Chloro-3-pyridyl | A-1 | H | COCH2OCH2C6H5 |
| 578-544 | 3-pyridyl | A-1 | H | COCH2OCH2C6H5 |
| 1-703 | 6-Chloro-3-pyridyl | A-1 | H | SOCF3 |
| 1-707 | 6-Chloro-3-pyridyl | A-1 | H | SO2OF3 |
| 1-708 | 6-Chloro-3-pyridyl | A-1 | H | SOCH3 |
| 1-692 | 6-Chloro-3-pyridyl | A-1 | H | P(=O)(OEt)2 |
| 1-700 | 6-Chloro-3-pyridyl | A-1 | H | P(=S)(SEt)2 |
| 1-701 | 6-Chloro-3-pyridyl | A-1 | H | P(=S)(S-n-propyl)2 |
| 1-702 | 6-Chloro-3-pyridyl | A-1 | H | P(=S)(S-isopropyl)2 |
| 1-646 | 6-Chloro-3-pyridyl | A-1 | H | COO-iso-Pr |
| 1-645 | 6-Chloro-3-pyridyl | A-1 | H | COOCH2C6H5 |
| 1-643 | 6-Chloro-3-pyridyl | A-1 | H | COC6F5 |
| 2-643 | 2-Chloro-5-thiazolyl | A-1 | H | COC6F5 |

TABLE 4

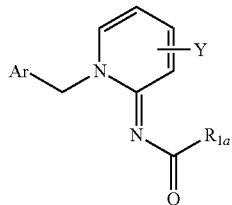

| compound No. | Ar | R1a | Y |
|---|---|---|---|
| P212 | 6-chloro-3-pyridyl | CF3 | H |
| P213 | 2-chloro-5-thiazolyl | CF3 | H |
| P214 | 6-chloro-3-pyridyl | OCH3 | H |
| P215 | 6-chloro-3-pyridyl | CF3 | 5-Cl |
| P216 | 6-chloro-3-pyridyl | CF3 | 5-F |
| P217 | 6-chloro-3-pyridyl | CF3 | 4-Cl |
| P218 | 2-chloro-5-thiazolyl | CF3 | 5-Cl |
| P219 | 2-chloro-5-thiazolyl | CF3 | 5-F |
| P220 | 2-chloro-5-thiazolyl | CF3 | 4-Cl |
| P221 | 6-chloro-3-pyridyl | CF3 | 3-Me |
| P222 | 6-chloro-3-pyridyl | CF3 | 4-Me |
| P223 | 6-chloro-3-pyridyl | CF3 | 5-Me |
| P224 | phenyl | CF3 | H |
| P225 | 4-chlorophenyl | CF3 | H |
| P226 | 3-pyridyl | CF3 | H |
| P227 | 6-chloro-5-fluoro-3-pyridyl | CF3 | H |
| P228 | 6-trifluoromethyl-3-pyridyl | CF3 | H |
| P229 | 6-fluoro-3-pyridyl | CF3 | H |
| P230 | 5,6-dichloro-3-pyridyl | CF3 | H |
| P231 | 6-bromo-3-pyridyl | CF3 | H |
| P232 | 6-chloro-3-pyridyl | CF3 | 4-F |
| P233 | 6-chloro-3-pyridyl | CF3 | 3-F |
| P234 | 6-chloro-3-pyridyl | CHCl2 | H |
| P235 | 6-chloro-3-pyridyl | CCl3 | H |
| P236 | 6-chloro-3-pyridyl | CH2Cl | H |
| P238 | 6-chloro-3-pyridyl | CHF2 | H |
| P239 | 6-chloro-3-pyridyl | CF2Cl | H |
| P240 | 6-chloro-3-pyridyl | CHClBr | H |
| P241 | 6-chloro-3-pyridyl | CHBr2 | H |
| P242 | 6-chloro-3-pyridyl | CF2CF3 | H |
| P243 | 2-chloro-5-pyrimidinyl | CF3 | H |
| P244 | 6-chloro-3-pyridyl | CH2Br | H |

Examples of more preferred compounds include N-[1-((6-chloropyridin-3-yl)methyl)pyridin-2(1H)-ylidene]-2,2,2-trifluoroacetamide (Compound P212) and N-[1-((6-chloropyridin-3-yl)methyl)pyridin-2(1H)-ylidene]-2,2,2-trifluoroethanethioamide (Compound 1-20), N-[1-((6-chloropyridin-3-yl)methyl)pyridin-2(1H)-ylidene]-2,2,2-trifluoro-N'-isopropylacetimidamide (Compound 1-45).

In addition, in the present invention, an acid addition salt of a iminopyridine derivative represented by Formula (I) (preferably, an agriculturally and zootechnically acceptable acid addition salt) may also be used, and examples thereof include an acid addition salt such as hydrochloride, nitrate, sulfate, phosphate, or acetate and the like.

In the present invention, examples of honeybees (*Apis*) include *Bombus, Meliponini, Apis dorsata, Apis dorsata laboriosa, Apis florea, Apis andreniformis, Apis mellifera, Apis cerana, Apis koschevnikovi*, and the like. Among them, preferable are *Apis mellifera* and *Apis cerana*. Moreover, in the present invention, when mentioned, honeybees include all members in a population of worker bees, drones, eggs, larvae, pupas, and queen bees.

Examples of honeybee parasitic pests include honeybee microsporidia (*Nosema apis*), *Varroa destructor, Varroa jacobsoni, Acarapis woodi*, honeybee *Tropilaelaps, Aethina tumida, Achroia innotata, Galleria mellonella* (wax moth), and the like. Among them, preferable are *Varroa destructor, Varroa jacobsoni*, honeybee *Tropilaelaps*, and *Acarapis woodi*.

Examples of a plant serving as a honey source of honeybees include Fagaceae (*Castanea, Castanopsis*), Magnoliaceae (*Liriodendroidae*), Theaceae (*Camellia japonica, Eurya japonica, Camellia sinensis*), Saxifragaceae (*Deutzia crenata*), Rosaceae (*Prunus salicina, Prunus mume, Prunus persica, Prunus serrulata, Prunus avium, Eriobotrya japonica, Malus pumila, Pyrus pyrifolia, Fragariaxananassa*), Fabaceae (*Wisteria floribunda, Styphnolobium japonicum, Robinia pseudoacacia, Lespedeza, Trifolium, Astragalus sinicus, Vigna*), Euphorbiaceae (*Mallotus japonicus*), Rutaceae (*Zanthoxylum ailanthoides, Phellodendron amurensis, Fortunella, Citrus*), Anacardiaceae (*Toxicodendron vernicifluum, Rhus javanica, Toxicodendron succedaneum*),

*Hippocastanaceae* (*Aesculus*), *Aquifoliaceae* (*Ilex rotunda, Ilex integra, Ilex serrata*), *Rhamnaceae* (*Hovenia dulcis*), *Tiliaceae* (*Tilia japonica*), *Cornaceae* (*Swida controversa*), *Araliaceae* (*Aralia elata, Eleutherococcus sciadophylloides, Kalopanax septemlobus*), *Clethraceae* (*Clethra*), *Ebenaceae* (*Diospyros kaki*), *Styracaceae* (*Styrax japonica*), *Oleaceae* (*Ligustrum japonicum, Ligustrum obtusifolium*), *Caprifoliaceae* (*Abelia x grandiflora, Abelia*), *Araceae* (*Acorus calamus*), *Polygonaceae* (*Fallopia japonica, Fagopyrum esculentum*), *Brassicaceae* (*Brassica rapa, Brassica oleracea*), *Cucurbitaceae* (*Sicyos angulatus, Cucurbita, Citrullus lanatus, Cucumis melo*), *Onagraceae* (*Oenothera tetraptera*), *Asteraceae* (thistles, *Bidens, Taraxacum, Solidago canadensis, Cosmos, Asteroideae*), *Crassulaceae* (*Phedimus aizoon*), *Vitaceae* (*Cayratia japonica*), and the like.

A honeybee parasitic pest control agent of the present invention may be used alone, or as a honeybee parasitic pest control composition mixed with another pest control agent, or a mixture with another pest control agent when used. Examples of such usable other pest control agents include pest control agents other than the compound represented by Formula (I) and acid addition salts thereof. The examples are an insecticide, a fungicide, a miticide, a herbicide, a plant growth regulator, a control agent for animal parasites, and the like. Specific examples of the other pest control agents include fluvalinate, flumethrin, amitraz, cymiazole, coumaphos, etoxazole, formic acid, sucrose acid esters, fenpyroxymate, acrinathrin, thymol, organic acids such as β-acid derived from hop, and the like.

The honeybee parasitic pest control agent and the honeybee parasitic pest control composition used in the present invention can be applied by spraying, dipping, coating, smoking, applying, drenching, granule applications, and the like. Specifically, the honeybee parasitic pest control agent and the honeybee parasitic pest control composition may be used as follows. An undiluted stock solution of honeybee parasitic pest control agent and the honeybee parasitic pest control composition or a solution thereof diluted with water or an appropriate solvent may be directly sprayed onto honeybees and/or a hive thereof such that an active ingredient in the solution is applied in an effective amount. Alternatively, a paper or tape material, such as a sheet, processed into an appropriate shape (examples of the material include plastic, polyvinyl chloride, polyvinylidene chloride, polyethylene, polypropylene, polyurethane, polyvinylpyrrolidone, polyester, nylon, paraffin, tree bark, tree piece, and the like) may be dipped into, coated with, or kneaded with the stock solution or the solution diluted with water or an appropriate solvent such that the active ingredient is applied in the effective amount; then, the paper or tape material may be attached inside the hive or around the hive to bring honeybees into contact with the paper or tape material.

Moreover, in order to control honeybee parasitic pests, the honeybee parasitic pest control agent and/or the honeybee parasitic pest control composition containing the active ingredient may also be used in a method by which the honeybee parasitic pest control agent and/or the honeybee parasitic pest control composition are mixed with water or a feed such that the active ingredient is applied in the effective amount; and the active ingredient penetrates honeybees via water absorption, intake, or the like. Further, the following method may also be used: a plant serving as the honey source of honeybees is subjected to a chemical treatment by foliar treatment, seed treatment, nursery tray treatment, soil treatment, trunk injection, or trunk coating, using the stock solution of the honeybee parasitic pest control agent and/or the honeybee parasitic pest control composition containing the active ingredient or the solution diluted with water or an appropriate solvent, such that the active ingredient is applied in the effective amount; honeybees visiting flowers of the plant treated with the chemical absorb the chemical (active ingredient); and the honeybees come into contact with an untreated honeybee group in a hive, so that the chemical (active ingredient) is impregnated into the hive.

According to Nouyaku Kagaku Yougo Jiten (Terminological Dictionary of Agrochemical Science) (published in 1994 by Japan Plant Protection Association), the foliar treatment is a chemical treatment on a leaf or the crown of a plant. The seed treatment is an application (treatment) of a chemical or the like on a seed, a seed tuber, a bulb, or the like. The seed treatment is referred to as a chemical application to seeds in general. The soil treatment is an application of a chemical on the soil surface, or an injection or mixing into soil. The soil treatment is referred to as a chemical application to soil in general. The trunk injection is an application method by which a chemical having penetrating and migrating property is injected into a trunk or a root to thereby control a pest on the tree, wither a thicket to death, or for other purposes. The trunk coating is coating of a trunk (bark) of a tree such as a fruit tree with a chemical, and is also referred to as a bark treatment, by which a trunk of a tree is coated with a chemical having penetrating and migrating property to thereby control a pest, a trunk is coated with an adhesive to thereby capture a pest to death, a trunk is coated with a repellent to thereby protect the bark and the like from feeding damage by harmful animals, or for other purposes.

In addition, a nursery tray refers to a tray such as a cell nursery tray for raising seedlings of a plant. The nursery tray treatment is an application or irrigation of a chemical to a cell tray during seedling before transplanted to a field.

An effective concentration or an effective amount of the active ingredient, that is, the compound represented by Formula (I) and/or acid addition salts thereof contained in the honeybee parasitic pest control agent of the present invention and the honeybee parasitic pest control composition of the present invention is 0.000001% to 0.1% in the case where the chemical is directly sprayed to honeybees or a hive thereof; 0.01% to 50% of the weight of a material such as a sheet in the case where the material is dipped into or is coated with the chemical; 0.000001% to 0.1% of water or a feed in the case where the active ingredient penetrates honeybees via water absorption, intake, or the like; and preferably 0.1 g to 10 kg, more preferably 1 g to 1 kg, per 10 ares of cultivated land in the case of the plant foliar treatment. In the case of the seed treatment, the effective amount is preferable 1 g to 10 kg, more preferably 10 g to 1 kg, per 10 kg of the seed. Moreover, in the case of the nursery tray treatment, the effective amount is preferably 0.01 g to 10 g, more preferably 0.1 g to 1 g, per nursery tray. In the case of the soil treatment, the effective amount is preferably 0.1 g to 10 kg, more preferably 1 g to 1 kg, per 10 ares of cultivated land. In the case of the trunk injection or the trunk coating, the effective amount is preferably 0.01 g to 1 kg, more preferably 0.1 g to 100 g, per tree.

The present invention can provide the honeybee parasitic pest control agent and the honeybee parasitic pest control composition usually as a preparation in any dosage form of emulsifiable concentrates, liquid formulations, suspensions, wettable powders, flowables, dust, granules, capsules, tablets, oils, sheet preparation, aerosols, fumigants, and the like, by mixing at least one of the compound represented by Formula (I) and acid addition salts thereof, or at least one of the compound represented by Formula (I) and acid addition salts thereof and at least one of other pest control agents, with a pharmaceutically acceptable carrier such as appropriate solid carrier, liquid carrier, gaseous carrier, surfactant, or dispersant. The method for preparing these forms is not particularly limited, and a form can be selected depending on the use, and formulated according to a technique usable in general pesticide preparation.

Examples of the pharmaceutically acceptable carrier of the present invention include carriers such as a solid carrier, a liquid carrier, and a gaseous carrier; surfactants; dispersants; adjuvants, and the like.

Examples of the solid carrier include talc, bentonite, clay, kaolin, diatomaceous earth, vermiculite, white carbon, calcium carbonate, and the like.

Examples of the liquid carrier include alcohols such as methanol, n-hexanol, and ethylene glycol; ketones such as acetone, methyl ethyl ketone, and cyclohexanone; aliphatic hydrocarbons such as n-hexane, kerosene, and lamp oil; aromatic hydrocarbons such as toluene, xylene, and methyl naphthalene; ethers such as diethyl ether, dioxane, and tetrahydrofuran; esters such as ethyl acetate; nitriles such as acetonitrile and isobutyl nitrile; acid amides such as dimethylformamide and dimethylacetamide; vegetable oils such as soybean oil and cottonseed oil; dimethyl sulfoxide; water; and the like.

Further, examples of the gaseous carrier include LPG, air, nitrogen, carbonic acid gas, dimethyl ether, and the like.

As the surfactant or dispersant for emulsification, dispersion, spreading and the like, it is possible to use, for example, alkylsulfate esters, alkyl (aryl) sulfonates, polyoxyalkylene alkyl (aryl) ethers, polyhydricalcohol esters, lignin sulfonates or the like.

In addition, as the adjuvant for improving the properties of the preparation, it is possible to use, for example, carboxymethylcellulose, gum arabic, polyethylene glycol, calcium stearate or the like.

The aforementioned carriers such as solid carriers, liquid carriers, gaseous carriers, surfactants, dispersants and adjuvant may be used either alone or in combination, if necessary.

The content of active ingredients in the preparation is not particularly limited, but is usually in the range of 1 to 75% by weight for the emulsifiable concentrate, 0.3 to 25% by weight for the dust, 1 to 90% by weight for the wettable powder, and 0.5 to 10% by weight for the granular formulation.

EXAMPLES

Preparation Example 1

Wettable Powder

| | |
|---|---|
| Compound P212 | 10% by weight |
| Clay | 70% by weight |
| White carbon | 2% by weight |
| Diatomaceous earth | 13% by weight |
| Calcium ligninsulfonate | 4% by weight |
| Sodium lauryl sulfate | 1% by weight |

The ingredients were homogeneously mixed and ground to obtain wettable powder.

Preparation Example 2

Water Dispersible Granule

| | |
|---|---|
| Compound P212 | 10% by weight |
| Clay | 80% by weight |
| Dextrin | 5% by weight |
| Alkyl maleate copolymer | 4% by weight |
| Sodium lauryl sulfate | 1% by weight |

The ingredients were homogeneously ground and mixed, water was added thereto to knead the ingredients thoroughly and then the mixture was granulated and dried to obtain water dispersible granules.

Preparation Example 3

Flowables

| | |
|---|---|
| Compound 1-20 | 5% by weight |
| POE polystyrylphenyl ether sulfate | 5% by weight |
| Propylene glycol | 6% by weight |
| Bentonite | 1% by weight |
| 1% xanthan-gum aqueous solution | 3% by weight |
| PRONALEX-300 (TOHO Chemical Industry Co., Ltd.) | 0.05% by weight |
| ADDAC827 (KI Chemical Industry Co., Ltd.) | 0.02% by weight |
| Water | added to 100% by weight |

All the ingredients except for the 1% xanthan-gum aqueous solution and a suitable amount of water were premixed together from the blending, and the mixture was then ground by a wet grinder. Thereafter, the 1% xanthan-gum aqueous solution and the remaining water were added thereto to obtain 100% by weight of flowables.

Preparation Example 4

Emulsifiable Concentrate

| | |
|---|---|
| Compound P212 | 2% by weight |
| N,N-dimethylformamide | 20% by weight |
| Solvesso 150 (Exxon Mobil Corporation) | 68% by weight |
| Polyoxyethylene alkyl aryl ether | 10% by weight |

The ingredients were homogeneously mixed and dissolved to obtain an emulsifiable concentrate.

Preparation Example 5

Dust

| | |
|---|---|
| Compound P212 | 0.5% by weight |
| Clay | 61.5% by weight |
| Talc | 37% by weight |
| Calcium stearate | 1% by weight |

The ingredients were homogeneously mixed to obtain dust.

Preparation Example 6

DL Dust

| | |
|---|---|
| Compound P212 | 1% by weight |
| DL clay | 96.5% by weight |
| White carbon | 2% by weight |
| Light liquid paraffin | 0.5% by weight |

The ingredients were homogeneously mixed to obtain dust.

Preparation Example 7

Microgranule Fine F

| | |
|---|---|
| Compound P212 | 1% by weight |
| Carrier | 95% by weight |
| White carbon | 2% by weight |
| Hisol SAS-296 | 2% by weight |

The ingredients were homogeneously mixed to obtain Microgranule fine F.

Preparation Example 8

Granules

| | |
|---|---|
| Compound 1-20 | 2% by weight |
| Bentonite | 40% by weight |
| Talc | 10% by weight |
| Clay | 46% by weight |
| Calcium ligninsulfonate | 2% by weight |

The ingredients were homogeneously ground and mixed, water was added thereto to knead the ingredients thoroughly, and then the mixture was granulated and dried to obtain granules.

Preparation Example 9

Microcapsules

| | |
|---|---|
| Compound 1-20 | 2% by weight |
| Urethane resin | 25% by weight |
| Sodium salt of naphthalene sulfonic acid formalin condensate | 5% by weight |
| 1,2-Benzisothiazolin-3-one | 0.2% by weight |
| Water | 67.8% by weight |

Microcapsules were obtained by forming a urethane resin coating on the surface of particles of the compound of the present invention by an interfacial polymerization method.

Preparation Example 10

Sheets

| | |
|---|---|
| Compound P212 | 10% by weight |
| oil | 10% by weight |
| Polyvinyl chloride | 80% by weight |

The compound of the present invention and oil were mixed to obtain a mixture, sheets were obtained by surface of the Polyvinyl chloride was immersed in the mixture.

Preparation Example 11

Sheets

| | |
|---|---|
| Compound P212 | 10% by weight |
| Phthalic ester | 30% by weight |
| oil | 5% by weight |
| Polyvinyl chloride | 55% by weight |

The ingredients were mixed and formed into a sheet-shape to obtain sheets.

Examples of Biological Tests

Test Example 1

Pest Control Test of *Varroa destructor*

After anesthesized with carbonic acid gas, adults of *Apis mellifera* infected with *Varroa destructor* were subjected to a chemical treatment by applying the abdomens with an acetone solution of the compound according to the present invention at predetermined concentrations using a micro applicator. After the treatment, *Apis mellifera* were transferred into a plastic case and left to stand in a thermostatic chamber under dark at 25° C. During the test period, 50% sucrose water absorbed to absorbent cotton was provided as a bait.

Forty eight hours after the chemical treatment, the number of *Apis mellifera* survived and the number of parasitic *Varroa destructor* were examined. The mortality of the honeybees and the preventive value against *Varroa destructor* were calculated by the following equations.

Mortality(%)={((100−survival rate in chemical treated plot)−(100−survival rate in acetone treated plot))/(100−mortality in acetone treated plot)}×100

Preventive value={(parasitism rate in untreated plot−parasitism rate in chemical treated plot)/(parasitism rate in untreated plot)}×100

As a result, when *Apis mellifera* infected with *Varroa destructor* were treated with 10 μg of the compound according to the present invention, a high preventive value was shown against *Varroa destructor*, and no *Apis mellifera* were killed. Commercially available fluvalinate even at a smaller application dose of 5 μg than that of the compound according to the present invention showed a mortality as high as 64%. In other words, it was confirmed that the compound according to the present invention acts as a chemical having both high efficacy against honeybee parasitic pests and high safety to honeybees.

TABLE 5

Mortality of honeybees

| Chemical name | Application dose (μg) | Mortality (%) |
|---|---|---|
| Acetone treatment | — | 0 |
| Compound P212 | 10 | 0 |
| Fluvalinate | 5 | 64 |

TABLE 6

Preventive value against *Varroa destructor*

| Chemical name | Application dose (μg) | Preventive value |
|---|---|---|
| Compound P212 | 10 | 100 |

Test Example 2

Pest Control Test of *Varroa destructor*

After anesthesized with carbonic acid gas, adults of *Apis mellifera* collected from a hive were grouped in test cages such that there were 10 to 20 heads per cage. Thereafter, the *Apis mellifera* were subjected to a chemical treatment by dipping the abdomens into an acetone solution of the compound according to the present invention at predetermined concentrations. After the *Apis mellifera* air-dried, the recovery of the *Apis mellifera* from the anesthesia was confirmed. Then, the cages were lidded to leave the *Apis mellifera* to stand in a thermostatic chamber under dark at 25° C. Note that 50% sucrose water absorbed to absorbent cotton was provided as a bait during the test period.

The number of *Apis mellifera* survived at 72 hours after the chemical treatment as well as the numbers of *Varroa destructor* parasitizing the *Apis mellifera* before the chemical treatment and at 72 hours after the chemical treatment were examined. The mortality and the parasitism rate were calculated by the following equations. The test was conducted in duplicate.

Mortality(%)={((100−survival rate in chemical treated plot)−(100−survival rate in acetone treated plot))/(100−mortality in acetone treated plot)}×100

Parasitism rate(%)=(number of heads of honeybees parasitized by *Varroa destructor*/number of honeybees survived)×100

As a result, it was confirmed that dipping *Apis mellifera* in 10 ppm of the compound according to the present invention sufficiently reduces the parasitism rate by *Varroa destructor*.

TABLE 7

Mortality of honeybees

| Chemical name | Rate (ppm) | Mortality at 72 hours after treatment (%) |
|---|---|---|
| Acetone treatment | — | 0 |
| compound P212 | 10 | 0 |
| compound 1-20 | 10 | 0 |

TABLE 8

Parasitism rate by *Varroa destructor*

| Chemical name | Rate (ppm) | Parasitism rate before treatment (%) | Parasitism rate at 72 hours after treatment (%) | Change in parasitism rate (%)* |
|---|---|---|---|---|
| Acetone treatment | — | 48 | 45 | −6 |
| Compound P212 | 10 | 17 | 10 | −41 |
| Compound 1-20 | 10 | 51 | 23 | −55 |

*{100 − (parasitism rate at 72 hours after treatment/parasitism rate before treatment) × 100}

[Industrial Applicability]

The pest control agent and the composition of the present invention as well as the pest control method using these in a throughput of the active ingredient as high as 10 μg per head of an adult do not show toxicity to honeybees but show high pest control effects on honeybee parasitic mites. Therefore, the present invention can greatly contribute to honeybee parasitic pest control.

What is claimed is:

1. A pest control method for honeybee parasitic pests, wherein the method uses as a honeybee parasitic pest control agent comprising:
at least one compound represented by the following Formula (I) or acid addition salts thereof as an active ingredient

(I)

[in the formula (I), Ar represents a phenyl group which may be substituted, a 5- to 6-membered heterocycle which may be substituted, or a 4- to 10-membered heterocycloalkyl group, A represents a 5- to 10-membered heterocycle having a unsaturated bond including one or more nitrogen atoms, and has an imino group substituted with an R group at a position adjacent to the nitrogen atom present on the cycle, Y represents a hydrogen atom, a halogen atom, a hydroxyl group, a C1 to C6 alkyl group which may be substituted with a halogen atom, a C1 to C6 alkyloxy group which may be substituted with a halogen atom, a cyano group, or a nitro group, and R represents any one of groups represented by the following Formulae (a) to (e), (y) or (z),

(a)

(b)

(c)

-continued

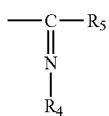
(d)

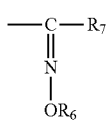
(e)

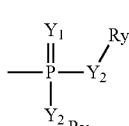
(y)

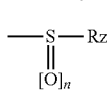
(z)

here, R₁ represents a hydrogen atom, a substituted C1 to C6 alkyl group, a C2 to C6 alkenyl group which may be substituted with a halogen atom, a C2 to C6 alkynyl group which may be substituted with a halogen atom, or a pentafluorophenyl group, R₂ represents a C1 to C6 alkyl group which may be substituted with a halogen atom, an unsubstituted C3 to C6 branched or cyclic alkyl group, a C2 to C6 alkenyl group which may be substituted with a halogen atom, a C2 to C6 alkynyl group which may be substituted with a halogen atom, a substituted or unsubstituted (C6 to C10) aryl group, a substituted or unsubstituted 5- to 10-membered heterocycle, or a substituted or unsubstituted benzyl group, R₃ represents a C1 to C6 alkyl group which may be substituted with a halogen atom, a C2 to C6 alkenyl group which may be substituted with a halogen atom, a C2 to C6 alkynyl group which may be substituted with a halogen atom, a substituted or unsubstituted (C6 to C10) aryl group, a substituted or unsubstituted (C6 to C10) aryl (C1 to C6) alkyl group, a substituted or unsubstituted (C6 to C10) aryl (C2 to C6) alkenyl group, a substituted or unsubstituted (C6 to C10) aryl (C2 to C6) alkynyl group, a substituted or unsubstituted phenoxy (C1 to C6) alkyl group, a substituted or unsubstituted phenoxy (C2 to C6) alkenyl group, a substituted or unsubstituted phenoxy (C2 to C6) alkynyl group, a substituted or unsubstituted 5- to 10-membered heterocycle, a substituted or unsubstituted 5- to 10-membered heterocycle (C1 to C6) alkyl group, a substituted or unsubstituted 5- to 10-membered heterocycle (C2 to C6) alkenyl group, a substituted or unsubstituted 5- to 10-membered heterocycle (C2 to C6) alkynyl group, a (C1 to C4) alkoxy (C1 to C5) alkyl group, a (C1 to C4) alkoxy (C2 to C5) alkenyl group, a (C1 to C4) alkoxy (C2 to C5) alkynyl group, a (C1 to C4) alkylthio (C1 to C5) alkyl group, a (C1 to C4) alkylthio (C2 to C5) alkenyl group, or a (C1 to C4) alkylthio (C2 to C5) alkynyl group, R₄ represents a hydrogen atom, a formyl group, a C1 to C18 alkyl group which may be substituted, a C2 to C6 alkenyl group which may be substituted with a halogen atom, a C2 to C6 alkynyl group which may be substituted with a halogen atom, a substituted or unsubstituted (C6 to C10) aryl group, a substituted or unsubstituted (C6 to C10) aryl (C1 to C6) alkyl group, a substituted or unsubstituted (C6 to C10) aryl (C2 to C6) alkenyl group, a substituted or unsubstituted (C6 to C10) aryl (C2 to C6) alkynyl group, a substituted or unsubstituted phenoxy (C1 to C6) alkyl group, a substituted or unsubstituted phenoxy (C2 to C6) alkenyl group, a substituted or unsubstituted phenoxy (C2 to C6) alkynyl group, a substituted or unsubstituted 5- to 10-membered heterocycle, a substituted or unsubstituted 5- to 10-membered heterocycle (C1 to C6) alkyl group, a substituted or unsubstituted 5- to 10-membered heterocycle (C2 to C6) alkenyl group, a substituted or unsubstituted 5- to 10-membered heterocycle (C2 to C6) alkynyl group, a (C1 to C4) alkoxy (C1 to C5) alkyl group, a (C1 to C4) alkoxy (C2 to C5) alkenyl group, a (C1 to C4) alkoxy (C2 to C5) alkynyl group, a (C1 to C4) alkylthio (C1 to C5) alkyl group, a (C1 to C4) alkylthio (C2 to C5) alkenyl group, a (C1 to C4) alkylthio (C2 to C5) alkynyl group, or a group represented by the following Formulae (f) to (n)

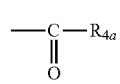
(f)

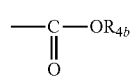
(g)

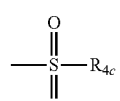
(h)

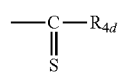
(i)

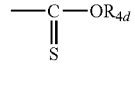
(j)

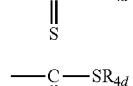
(k)

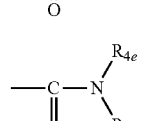
(l)

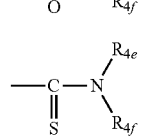
(m)

(n)

here, $R_{4a}$, $R_{ob}$ and $R_{oc}$ represent a C1 to C6 alkyl group which may be substituted with a halogen atom, a C2 to C6 alkenyl group which may be substituted with a halogen atom, a C2 to C6 alkynyl group which may be substituted with a halogen atom, a substituted or unsubstituted (C6 to C10) aryl group, a substituted or unsubstituted (C6 to C10) aryl (C1 to C6) alkyl group, a substituted or unsubstituted (C6 to C10) aryl (C2 to C6) alkenyl group, a substituted or unsubstituted (C6 to C10) aryl (C2 to C6) alkynyl group, a substituted or unsubstituted phenoxy (C1 to C6) alkyl group, a substituted or unsubstituted phenoxy (C2 to C6) alkenyl group, a substituted or unsubstituted phenoxy (C2 to C6) alkynyl group, a substituted or unsubstituted 5- to 10-membered heterocycle, a substituted or unsubstituted 5- to 10-membered heterocycle (C1 to C6) alkyl group, a substituted or unsubstituted 5- to 10-membered heterocycle (C2 to C6) alkenyl group, a substituted or unsubstituted 5- to 10-membered heterocycle (C2 to C6) alkynyl group, a (C1 to C4) alkoxy (C1 to C5) alkyl group, a (C1 to C4) alkoxy (C2 to C5) alkenyl group, a (C1 to C4) alkoxy (C2 to C5) alkynyl group, a (C1 to C4) alkylthio (C1 to C5) alkyl group, a (C1 to C4) alkylthio (C2 to C5) alkenyl group, or a (C1 to C4) alkylthio (C2 to C5) alkynyl group, $R_{4d}$ represents a C1 to C6 alkyl group which may be substituted with a halogen atom, a C2 to C6 alkenyl group which may be substituted with a halogen atom, a C2 to C6 alkynyl group which may be substituted with a halogen atom, a substituted or unsubstituted (C6 to C10) aryl group, or a substituted or unsubstituted 5- to 10-membered heterocycle, and $R_{4e}$ and $R_{4f}$ each independently represent a hydrogen atom, a C1 to C6 alkyl group which may be substituted with a halogen atom, a C2 to C6 alkenyl group which may be substituted with a halogen atom, a C2 to C6 alkynyl group which may be substituted with a halogen atom, a substituted or unsubstituted (C6 to C10) aryl group, or a substituted or unsubstituted 5- to 10-membered heterocycle, $R_5$ represents a C1 to C6 alkyl group which may be substituted with a halogen atom, a C2 to C6 alkenyl group which may be substituted with a halogen atom, a C2 to C6 alkynyl group which may be substituted with a halogen atom, a substituted or unsubstituted (C6 to C10) aryl group, a substituted or unsubstituted (C6 to C10) aryl (C1 to C6) alkyl group, a substituted or unsubstituted (C6 to C10) aryl (C2 to C6) alkenyl group, a substituted or unsubstituted (C6 to C10) aryl (C2 to C6) alkynyl group, a substituted or unsubstituted phenoxy (C1 to C6) alkyl group, a substituted or unsubstituted phenoxy (C2 to C6) alkenyl group, a substituted or unsubstituted phenoxy (C2 to C6) alkynyl group, a substituted or unsubstituted 5- to 10-membered heterocycle, a substituted or unsubstituted 5- to 10-membered heterocycle (C1 to C6) alkyl group, a substituted or unsubstituted 5- to 10-membered heterocycle (C2 to C6) alkenyl group, a substituted or unsubstituted 5- to 10-membered heterocycle (C2 to C6) alkynyl group, a (C1 to C4) alkoxy (C1 to C5) alkyl group, a (C1 to C4) alkoxy (C2 to C5) alkenyl group, a (C1 to C4) alkoxy (C2 to C5) alkynyl group, a (C1 to C4) alkylthio (C1 to C5) alkyl group, a (C1 to C4) alkylthio (C2 to C5) alkenyl group, or a (C1 to C4) alkylthio (C2 to C5) alkynyl group, $R_6$ represents a hydrogen atom, a formyl group, a O,O'—C1 to C4 alkyl phosphoryl group, a C1 to C18 alkyl group which may be substituted, a C2 to C6 alkenyl group which may be substituted with a halogen atom, a C2 to C6 alkynyl group which may be substituted with a halogen atom, a substituted or unsubstituted (C6 to C10) aryl group, a substituted or unsubstituted (C6 to C10) aryl (C1 to C6) alkyl group, a substituted or unsubstituted (C6 to C10) aryl (C2 to C6) alkenyl group, a substituted or unsubstituted (C6 to C10) aryl (C2 to C6) alkynyl group, a substituted or unsubstituted phenoxy (C1 to C6) alkyl group, a substituted or unsubstituted phenoxy (C2 to C6) alkenyl group, a substituted or unsubstituted phenoxy (C2 to C6) alkynyl group, a substituted or unsubstituted 5- to 10-membered heterocycle, a substituted or unsubstituted 5- to 10-membered heterocycle (C1 to C6) alkyl group, a substituted or unsubstituted 5- to 10-membered heterocycle (C2 to C6) alkenyl group, a substituted or unsubstituted 5- to 10-membered heterocycle (C2 to C6) alkynyl group, a (C1 to C4) alkoxy (C1 to C5) alkyl group, a (C1 to C4) alkoxy (C2 to C5) alkenyl group, a (C1 to C4) alkoxy (C2 to C5) alkynyl group, a (C1 to C4) alkylthio (C1 to C5) alkyl group, a (C1 to C4) alkylthio (C2 to C5) alkenyl group, a (C1 to C4) alkylthio (C2 to C5) alkynyl group, or a group represented by the following Formulae (o) to (x)

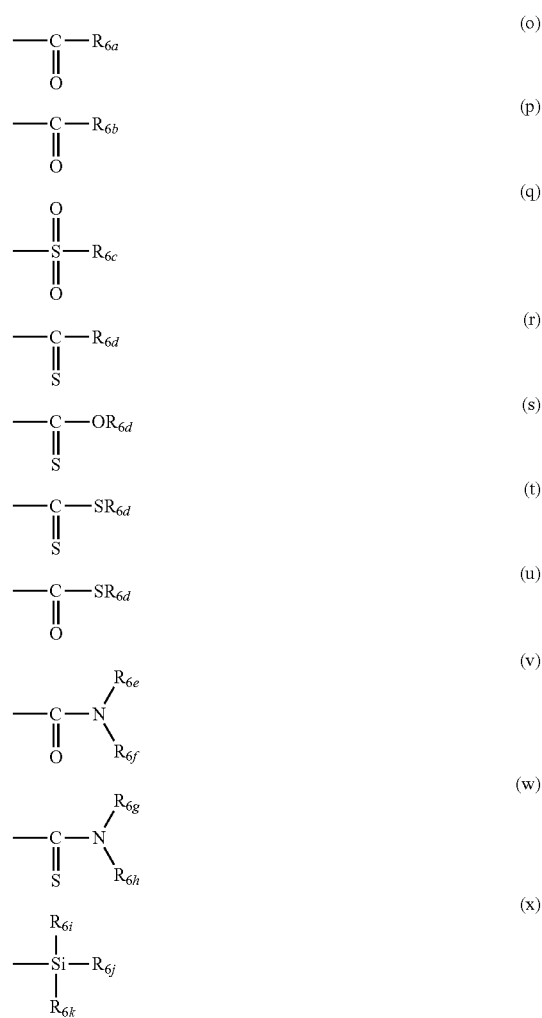

here, $R_{6a}$, $R_{6b}$ and $R_{6c}$ represent a C1 to C6 alkyl group which may be substituted with a halogen atom, a C2 to C6 alkenyl group which may be substituted with a halogen atom, a C2 to C6 alkynyl group which may be substituted with a halogen atom, a substituted or unsubstituted (C6 to C10) aryl group, a substituted or unsubstituted (C6 to C10) aryl (C1 to C6) alkyl group, a substituted or unsubstituted (C6 to C10) aryl (C2 to C6) alkenyl group, a substituted or unsubstituted (C6 to C10) aryl (C2 to C6) alkynyl group, a substituted or unsubstituted phenoxy (C1 to C6) alkyl group, a substituted or unsubstituted phenoxy (C2 to C6) alkenyl group, a substituted or unsubstituted phenoxy (C2 to C6) alkynyl group, a substituted or unsubstituted 5- to 10-membered heterocycle, a substituted or unsubstituted 5- to 10-membered heterocycle (C1 to C6) alkyl group, a substituted or unsubstituted 5- to 10-membered heterocycle (C2 to C6) alkenyl group, a substituted or unsubstituted 5- to 10-membered heterocycle (C2 to C6) alkynyl group, a (C1 to C4) alkoxy (C1 to C5) alkyl group, a (C1 to C4) alkoxy (C2 to C5) alkenyl group, a (C1 to C4) alkoxy (C2 to C5) alkynyl group, a (C1 to C4) alkylthio (C1 to C5) alkyl group, a (C1 to C4) alkylthio (C2 to C5) alkenyl group, or a (C1 to C4) alkylthio (C2 to C5) alkynyl group, $R_{6d}$ represents a C1 to C6 alkyl group which may be substituted with a halogen atom, a C2 to C6 alkenyl group which may be substituted with a halogen atom, a C2 to C6 alkynyl group which may be substituted with a halogen atom, a substituted or unsubstituted (C6 to C10) aryl group, or a substituted or unsubstituted 5- to 10-membered heterocycle, $R_{6e}$ and $R_{6f}$ each independently represent a hydrogen atom, a C1 to C6 alkyl group which may be substituted with a halogen atom, a C2 to C6 alkenyl group which may be substituted with a halogen atom, a C2 to C6 alkynyl group which may be substituted with a halogen atom, a (C1 to C4) alkoxy (C1 to C5) alkyl group, a (C1 to C4) alkylthio (C1 to C5) alkyl group, a substituted or unsubstituted (C6 to C10) aryl group, a substituted or unsubstituted (C6 to C10) aryl (C1 to C6) alkyl group, or a substituted or unsubstituted 5- to 10-membered heterocycle, $R_{6g}$ and $R_{6h}$ each independently represent a hydrogen atom, a C1 to C6 alkyl group which may be substituted with a halogen atom, a C2 to C6 alkenyl group which may be substituted with a halogen atom, a C2 to C6 alkynyl group which may be substituted with a halogen atom, a substituted or unsubstituted (C6 to C10) aryl group, or a substituted or unsubstituted 5- to 10-membered heterocycle, and $R_{6i}$, $R_{6j}$ and $R_{6k}$ each independently represent a hydrogen atom, a C1 to C6 alkyl group which may be substituted with a halogen atom, a C2 to C6 alkenyl group which may be substituted with a halogen atom, a C2 to C6 alkynyl group which may be substituted with a halogen atom, or a substituted or unsubstituted (C6 to C10) aryl group, and $R_7$ represents a C1 to C6 alkyl group which may be substituted with a halogen atom, a C2 to C6 alkenyl group which may be substituted with a halogen atom, a C2 to C6 alkynyl group which may be substituted with a halogen atom, a substituted or unsubstituted (C6 to C10) aryl group, a substituted or unsubstituted (C6 to C10) aryl (C1 to C6) alkyl group, a substituted or unsubstituted (C6 to C10) aryl (C2 to C6) alkenyl group, a substituted or unsubstituted (C6 to C10) aryl (C2 to C6) alkynyl group, a substituted or unsubstituted phenoxy (C1 to C6) alkyl group, a substituted or unsubstituted phenoxy (C2 to C6) alkenyl group, a substituted or unsubstituted phenoxy (C2 to C6) alkynyl group, a substituted or unsubstituted 5- to 10-membered heterocycle, a substituted or unsubstituted 5- to 10-membered heterocycle (C1 to C6) alkyl group, a substituted or unsubstituted 5- to 10-membered heterocycle (C2 to C6) alkenyl group, a substituted or unsubstituted 5- to 10-membered heterocycle (C2 to C6) alkynyl group, a (C1 to C4) alkoxy (C1 to C5) alkyl group, a (C1 to C4) alkoxy (C2 to C5) alkenyl group, a (C1 to C4) alkoxy (C2 to C5) alkynyl group, a (C1 to C4) alkylthio (C1 to C5) alkyl group, a (C1 to C4) alkylthio (C2 to C5) alkenyl group, or a (C1 to C4) alkylthio (C2 to C5) alkynyl group, $Y_1$ and $Y_2$ represent an oxygen atom or a sulfur atom, and may be the same or different, and $R_y$ represents a C1 to C6 alkyl group which may be substituted with a halogen atom, a C2 to C6 alkenyl group which may be substituted with a halogen atom, a C2 to C6 alkynyl group which may be substituted with a halogen atom, a substituted or unsubstituted (C6 to C10) aryl group, a substituted or unsubstituted (C6 to C10) aryl (C1 to C6) alkyl group, a substituted or unsubstituted (C6 to C10) aryl (C2 to C6) alkenyl group, a substituted or unsubstituted (C6 to C10) aryl (C2 to C6) alkynyl group, a substituted or unsubstituted phenoxy (C1 to C6) alkyl group, a substituted or unsubstituted phenoxy (C2 to C6) alkenyl group, a substituted or unsubstituted phenoxy (C2 to C6) alkynyl group, a substituted or unsubstituted 5- to 10-membered heterocycle, a substituted or unsubstituted 5- to 10-membered heterocycle (C1 to C6) alkyl group, a substituted or unsubstituted 5- to 10-membered heterocycle (C2 to C6) alkenyl group, or a substituted or unsubstituted 5- to 10-membered heterocycle (C2 to C6) alkynyl group, R, represents a C1 to C6 alkyl group which may be substituted with a halogen atom, a C2 to C6 alkenyl group which may be substituted with a halogen atom, a C2 to C6 alkynyl group which may be substituted with a halogen atom, a substituted or unsubstituted (C6 to C10) aryl group, a substituted or unsubstituted (C6 to C10) aryl (C1 to C6) alkyl group, a substituted or unsubstituted (C6 to C10) aryl (C2 to C6) alkenyl group, a substituted or unsubstituted (C6 to C10) aryl (C2 to C6) alkynyl group, a substituted or unsubstituted phenoxy (C1 to C6) alkyl group, a substituted or unsubstituted phenoxy (C2 to C6) alkenyl group, a substituted or unsubstituted phenoxy (C2 to C6) alkynyl group, a substituted or unsubstituted 5- to 10-membered heterocycle, a substituted or unsubstituted 5- to 10-membered heterocycle (C1 to C6) alkyl group, a substituted or unsubstituted 5- to 10-membered heterocycle (C2 to C6) alkenyl group, a substituted or unsubstituted 5- to 10-membered heterocycle (C2 to C6) alkynyl group, a (C1 to C4) alkoxy (C1 to C5) alkyl group, a (C1 to C4) alkoxy (C2 to C5) alkenyl group, a (C1 to C4) alkoxy (C2 to C5) alkynyl group, a (C1 to C4) alkylthio (C1 to C5) alkyl group, a (C1 to C4) alkylthio (C2 to C5) alkenyl group, or a (C1 to C4) alkylthio (C2 to C5) alkynyl group, and n represents 1 or 2].

2. The pest control method for honeybee parasitic pests according to claim 1, wherein the honeybee parasitic pests are any one of *Varroa destructor*, honeybee *Tropilaelaps*, and *Acarapis woodi*.

3. The pest control method for honeybee parasitic pests according to claim 1, comprising spraying the honeybee parasitic pest control agent diluted with water or without dilution to a hive of honeybees such that the active ingredient is applied in an effective amount.

4. The pest control method for honeybee parasitic pests according to claim 1, comprising bringing honeybees into contact with a paper or tape material having been dipped into or coated with the honeybee parasitic pest control agent such that the active ingredient is applied in an effective amount.

5. The pest control method for honeybee parasitic pests according to claim 1, comprising mixing the honeybee parasitic pest control agent with water or a feed such that the active ingredient is applied in the effective amount.

6. The pest control method for honeybee parasitic pests according to claim 1, comprising subjecting a plant to any one of foliar treatment, seed treatment, nursery tray treatment, soil treatment, trunk injection, and trunk coating, using the honeybee parasitic pest control agent diluted with water or without dilution, such that the active ingredient is applied in the effective amount to thereby control the honeybee parasitic pests.

7. The pest control method for honeybee parasitic pests according to claim 1, wherein the at least one compound comprises an amine derivative represented by the following Formula (Ia) or acid addition salts thereof:

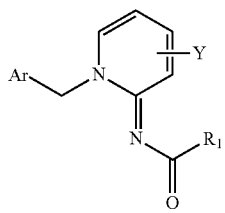

(Ia)

[here, Ar represents a pyridyl group which may be substituted with a halogen atom, a hydroxyl group, a C1 to C6 alkyl group which may be substituted with a halogen atom, a C1 to C6 alkyloxy group which may be substituted with a halogen atom, a cyano group, or a nitro group, or a pyrimidyl group which may be substituted with a halogen atom, a C1 to C4 alkyl group which may be substituted with a halogen atom, an alkyloxy group which may be substituted with a halogen atom, a hydroxyl group, a cyano group, or a nitro group, Y represents a hydrogen atom, a halogen atom, a hydroxyl group, a C1 to C6 alkyl group which may be substituted with a halogen atom, a C1 to C6 alkyloxy group which may be substituted with a halogen atom, a cyano group, or a nitro group, and $R_1$ represents a C1 to C6 alkyl group which is substituted with halogen].

8. The pest control method for honeybee parasitic pests according to claim 1, wherein the at least one compound comprises an amine derivative represented by the following Formula (Ic) or acid addition salts thereof:

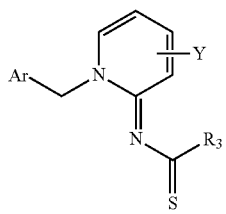

(Ic)

[here, Ar represents a pyridyl group which may be substituted with a halogen atom, a hydroxyl group, a C1 to C6 alkyl group which may be substituted with a halogen atom, a C1 to C6 alkyloxy group which may be substituted with a halogen atom, a cyano group, or a nitro group, or a pyrimidyl group which may be substituted with a halogen atom, a C1 to C4 alkyl group which may be substituted with a halogen atom, an alkyloxy group which may be substituted with a halogen atom, a hydroxyl group, a cyano group, or a nitro group, Y represents a hydrogen atom, a halogen atom, a hydroxyl group, a C1 to C6 alkyl group which may be substituted with a halogen atom, a C1 to C6 alkyloxy group which may be substituted with a halogen atom, a cyano group, or a nitro group, and $R_3$ represents a C1 to C6 alkyl group which is substituted with halogen].

9. The pest control method for honeybee parasitic pests according to claim 1, wherein ring A in Formula (I) represented by the following Formula:

is a ring with Formula (A-1):

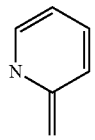

(A-1)

and Y is at least one of a hydrogen atom, a halogen atom and a cyano group.

10. The pest control method for honeybee parasitic pests according to claim 1, wherein R in Formula (I) is a group with Formula (c):

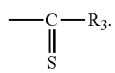

(c)

11. The pest control method for honeybee parasitic pests according to claim 1, wherein R in Formula (I) is a group with Formula (a):

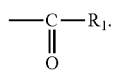

(a)

12. The pest control method for honeybee parasitic pests according to claim 1, wherein R in Formula (I) is a group with Formula (d):

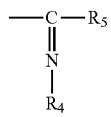

(d)

and $R_4$ represents a C1 to C18 alkyl group which may be substituted, a C2 to C6 alkenyl group which may be substituted with a halogen atom, a C2 to C6 alkynyl group which may be substituted with a halogen atom, a substituted or unsubstituted (C6 to C10) aryl group, a substituted or unsubstituted (C6 to C10) aryl (C1 to C6)

alkyl group, a substituted or unsubstituted (C6 to C10) aryl (C2 to C6) alkenyl group, a substituted or unsubstituted (C6 to C10) aryl (C2 to C6) alkynyl group, a substituted or unsubstituted phenoxy (C1 to C6) alkyl group, a substituted or unsubstituted phenoxy (C2 to C6) alkenyl group, a substituted or unsubstituted phenoxy (C2 to C6) alkynyl group, a substituted or unsubstituted 5- to 10-membered heterocycle, a substituted or unsubstituted 5- to 10-membered heterocycle (C1 to C6) alkyl group, a substituted or unsubstituted 5- to 10-membered heterocycle (C2 to C6) alkenyl group, a substituted or unsubstituted 5- to 10-membered heterocycle (C2 to C6) alkynyl group, a (C1 to C4) alkoxy (C1 to C5) alkyl group, a (C1 to C4) alkoxy (C2 to C5) alkenyl group, a (C1 to C4) alkoxy (C2 to C5) alkynyl group, a (C1 to C4) alkylthio (C1 to C5) alkyl group, a (C1 to C4) alkylthio (C2 to C5) alkenyl group, a (C1 to C4) alkylthio (C2 to C5) alkynyl group, and $R_5$ is a C1 to C6 alkyl group which may be substituted with a halogen atom, a C2 to C6 alkenyl group which may be substituted with a halogen atom, or a C2 to C6 alkynyl group which may be substituted with a halogen atom.

13. The pest control method for honeybee parasitic pests according to claim 1, wherein Ar is any one of a 6-chloro-3-pyridyl group, a 6-chloro-5-fluoro-3-pyridyl group, a 6-fluoro-3-pyridyl group, a 6-bromo-3-pyridyl group, and a 2-chloro-5-pyrimidyl group.

* * * * *